US011771739B2

(12) United States Patent
Hawiger et al.

(10) Patent No.: US 11,771,739 B2
(45) Date of Patent: Oct. 3, 2023

(54) METHODS AND COMPOSITIONS FOR TREATING MICROBIAL INFLAMMATION

(71) Applicants: VANDERBILT UNIVERSITY, Nashville, TN (US); THE UNITED STATES AS REPRESENTED BY THE DEPARTMENT OF VETERANS AFFAIRS, Washington, DC (US)

(72) Inventors: Jack Jacek Hawiger, Nashville, TN (US); Jozef Zienkiewicz, Nashville, TN (US); Ruth Ann Veach, Brentwood, TN (US); Yan Liu, Nashville, TN (US); Lukasz Wylezinski, Nashville, TN (US)

(73) Assignees: Vanderbilt University, Nashville, TN (US); The United States As Represented By The Department Of Veterans Affairs, Washington, DC (US)

( * ) Notice: Subject to any disclaimer, the term of this patent is extended or adjusted under 35 U.S.C. 154(b) by 0 days.

(21) Appl. No.: 16/622,469

(22) PCT Filed: Jun. 18, 2018

(86) PCT No.: PCT/US2018/037993
§ 371 (c)(1),
(2) Date: Dec. 13, 2019

(87) PCT Pub. No.: WO2018/232383
PCT Pub. Date: Dec. 20, 2018

(65) Prior Publication Data
US 2021/0145928 A1    May 20, 2021

Related U.S. Application Data

(60) Provisional application No. 62/521,159, filed on Jun. 16, 2017.

(51) Int. Cl.
*A61K 38/16* (2006.01)
*A61P 31/04* (2006.01)

(52) U.S. Cl.
CPC .............. *A61K 38/16* (2013.01); *A61P 31/04* (2018.01)

(58) Field of Classification Search
CPC ......... C07K 14/00; A61K 38/16; A61P 31/04; A61P 29/00; A61P 31/00
See application file for complete search history.

(56) References Cited

U.S. PATENT DOCUMENTS

| | | | |
|---|---|---|---|
| 6,495,518 B1 * | 12/2002 | Hawiger | A61P 29/00 514/1.2 |
| 7,553,929 B2 * | 6/2009 | Hawiger | A61K 47/62 530/317 |
| 9,303,000 B2 | 4/2016 | Sandanayaka et al. | |
| 2004/0235746 A1 | 11/2004 | Hawiger et al. | |
| 2011/0319323 A1 | 12/2011 | Schricker et al. | |
| 2017/0100454 A1 | 4/2017 | Hawiger et al. | |

FOREIGN PATENT DOCUMENTS

| WO | 1997/010818 | 3/1997 | |
|---|---|---|---|
| WO | 2013/112834 | 8/2013 | |
| WO | WO-2013112834 A1 * | 8/2013 | ........... A61K 31/496 |

OTHER PUBLICATIONS

Liu et al. "Suppression of Acute Lung Inflammation by Intracellular Peptide Delivery of a Nuclear Import Inhibitor", Molecular Therapy, 2009, 796-802 (Year: 2009).*
Veach et al. "Lethality in a Murine Model of Pulmonary Anthrax is Reduced by Combining Nuclear Transport Modifier with Antimicrobial Therapy", Plos One, 2012, pp. 1-6 (Year: 2012).*
O'Sullivan et al. ,"NF-KB and P38 Mapk Inhibition Improve Survival in Endotoxin Shock and in a Cecal Ligation and Puncture Model of Sepsis in Combination With Antibiotic Therapy", Journal of Surgical Research, 2009, pp. 46-53 (Year: 2009).*
EMD Millipore ,"NF-κb SN50, Cell-Permeable Inhibitor Peptide—Calbiochem", https://www.emdmillipore.com/US/en/product/NF-B-SN50-Cell-Permeable-Inhibitor-Peptide-Calbiochem, EMD_BIO-481480#anchor_PDS, accessed on May 13, 2022 (Year: 2022).*
Martinez et al., "Everything you need to know about inflammation", Medical News Today, 2020; https://www.medicalnewstoday.com/articles/248423 (Year: 2020).*
Extended EP Search Report dated Feb. 12, 2021, issued in related EP application No. 18817730.7, 13 pages.
Veach, R.A et al. "Survival, bacterial clearance and thrombocytopenia are improved in polymicrobial sepsis by targeting nuclear transport shuttles", Plos One 2017, vol. 12, No. 6, Jun. 19, 2017.
Angus DC, van der Poll T (2013) Severe sepsis and septic shock. N Engl J Med 369: 2063.
Baran-Marszak F, Feuillard J, Najjar I, Le Clorennec C, Bechet JM, Dusanter-Fourt I, et al. (2004) Differential roles of STAT1alpha and STAT1beta in fludarabine-induced cell cycle arrest and apoptosis in human B cells. Blood 104: 2475-2483.
Beutler B (2004) Innate immunity: an overview. Mol Immunol 40: 845-859.

(Continued)

*Primary Examiner* — Lianko G Garyu
(74) *Attorney, Agent, or Firm* — Meunier Carlin & Curfman LLC

(57) ABSTRACT

Disclosed are compositions and methods for treating microbial inflammation including its end-stage sepsis and conditions associated with the microbial inflammation such as thrombocytopenia and hypoglycogenemia. In one aspect, the compositions and methods disclosed herein can also be used to enhance clearance of microbes from infected tissues, organs, or systems in a subject. Also disclosed herein are compositions and methods for reducing levels of stress responsible transcription factors and metabolic transcription factors in a cell in a subject with microbial inflammation.

Figure 1:
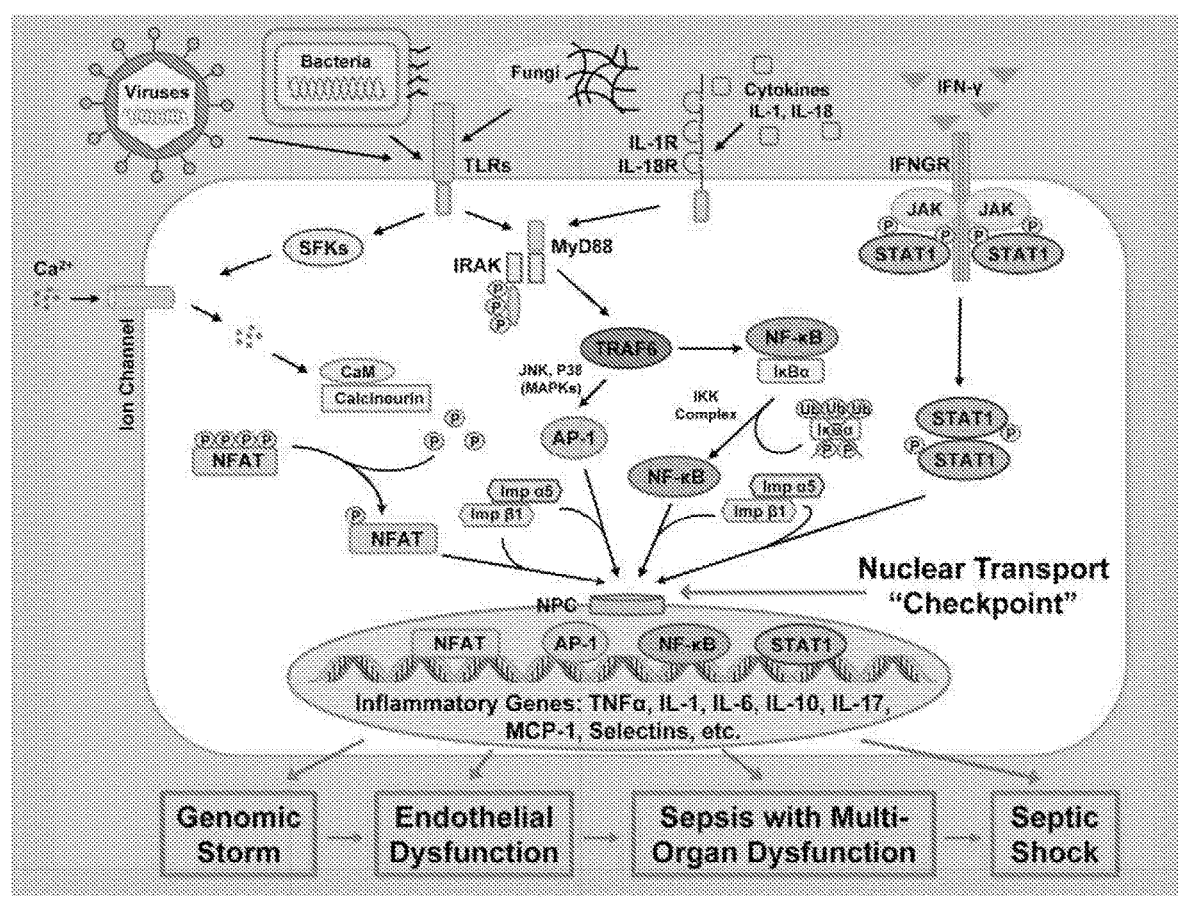

6 Claims, 6 Drawing Sheets
Specification includes a Sequence Listing.

(56) References Cited

OTHER PUBLICATIONS

Bohrer H, Qiu F, Zimmermann T, Zhang Y, Jllmer T, Mannel D, et al. (1997) Role of NFkappaB in the mortality of sepsis. J Clin Invest 100: 972-985.

Buckley CD, Gilroy DW, Serhan CN (2014) Proresolving lipid mediators and mechanisms in the resolution of acute inflammation. Immunity 40: 315-327.

Charalambous BM, Leung MH (2012) Pneumococcal sepsis and nasopharyngeal carriage. Curr Opin Pulm Med 18: 222-227.

Davis CE, Arnold K (1974) Role of meningococcal endotoxin in meningococcal purpura. J Exp Med 140: 159-171.

Deng M, Scott MJ, Loughran P, Gibson G, Sodhi C, Watkins S, et al. (2013) Lipopolysaccharide clearance, bacterial clearance, and systemic inflammatory responses are regulated by cell type-specific functions of TLR4 during sepsis. J Immunol 190: 5152-5160.

DiGiandomenico A, Veach RA, Zienkiewicz J, Moore DJ, Wylezinski LS, Hutchens MA, et al. (2014) The "genomic storm" induced by bacterial endotoxin is calmed by a nuclear transport modifier that attenuates localized and systemic inflammation. PLOS One 9: e110183.

Duerschmied D, Bode C, Ahrens I (2014) Immune functions of platelets. Thromb Haemost 112: 678-691.

Frazier WJ, Wang X, Wancket LM, Li XA, Meng X, Nelin LD, et al. (2009) Increased inflammation, impaired bacterial clearance, and metabolic disruption after gram-negative sepsis in Mkp-1-deficient mice. J Immunol 183: 7411-7419.

Haraldsen G, Kvale D, Lien B, Farstad IN, Brandtzaeg P (1996) Cytokine-regulated expression of E-selectin, intercellular adhesion molecule-1 (ICAM-1), and vascular cell adhesion molecule-1 (VCAM-1) in human microvascular endothelial cells. J Immunol 156: 2558-2565.

Hawiger J (2001) Innate immunity and inflammation: a transcriptional paradigm. Immunol Res 23: 99-109.

Hawiger J, Musser JM (2011) How to approach genome wars in sepsis? Crit Care 15: 1007.

Hawiger J, Veach RA, Zienkiewicz J (2015) New paradigms in sepsis: from prevention to protection of failing microcirculation. J Thromb Haemost 13: 1743-1756.

Herwig MC, Tsokos M, Hermanns MI, Kirkpatrick CJ, Müller AM (2013) Vascular Endothelial Cadherin Expression in Lung Specimens of Patients with Sepsis-Induced Acute Respiratory Distress Syndrome and Endothelial Cell Cultures. Pathobiology 80: 245-251.

Hui P, Cook DJ, Lim W, Fraser GA, Arnold DM (2011) The frequency and clinical significance of thrombocytopenia complicating critical illness: a systematic review. Chest 139: 271-278.

Jung TW, Hwang HJ, Hong HC, Choi HY, Yoo HJ, Baik SH, et al. (2014) Resolvin D1 reduces ER stress-induced apoptosis and triglyceride accumulation through JNK pathway in HepG2 cells. Mol Cell Endocrinol 391: 30-40.

Kishimoto TK, Jutila MA, Berg EL, Butcher EC (1989) Neutrophil Mac-1 and MEL-14 adhesion proteins inversely regulated by chemotactic factors. Science 245: 1238-1241.

Kroger C, Kary SC, Schauer K, Cameron AD (2016) Genetic Regulation of Virulence and Antibiotic Resistance in Acinetobacter baumannii. Genes (Basel) 8.

Kumar A, Roberts D, Wood KE, Light B, Parrillo JE, Sharma S, et al. (2006) Duration of hypotension before initiation of effective antimicrobial therapy is the critical determinant of survival in human septic shock. Crit Care Med 34: 1589-1596.

Langley RJ, Tsalik EL, van Velkinburgh JC, Glickman SW, Rice BJ, Wang C, et al. (2013) An integrated clinico-metabolomic model improves prediction of death in sepsis. Sci Transl Med 5: 195ra195.28.

Leeuwenberg JF, Smeets EF, Neefjes JJ, Shaffer MA, Cinek T, Jeunhomme TM, et al. (1992) E-selectin and intercellular adhesion molecule-1 are released by activated human endothelial cells in vitro. Immunology 77: 543-549.

Ley K (2003) The role of selectins in inflammation and disease. Trends Mol Med 9: 263-268.

Ley K, Bullard DC, Arbones ML, Bosse R, Vestweber D, Tedder TF, et al. (1995) Sequential contribution of L- and P-selectin to leukocyte rolling in vivo. J Exp Med 181: 669-675.

Liu D, Li C, Chen Y, Burnett C, Liu XY, Downs S, et al. (2004) Nuclear import of proinflammatory transcription factors is required for massive liver apoptosis induced by bacterial lipopolysaccharide. J Biol Chem 279: 48434-48442. .

Liu D, Liu XY, Robinson D, Burnett C, Jackson C, Seele L, et al. (2004) Suppression of Staphylococcal Enterotoxin B-induced Toxicity by a Nuclear Import Inhibitor. J Biol Chem 279: 19239-19246.

Liu G, Ye X, Miller EJ, Liu SF (2014) NF-kappaB-to-AP-1 switch: a mechanism regulating transition from endothelial barrier injury to repair in endotoxemic mice. Sci Rep 4: 5543.

Liu XY, Robinson D, Veach RA, Liu D, Timmons S, Collins RD, et al. (2000) Peptide-directed suppression of a pro-inflammatory cytokine response. J Biol Chem 275: 16774-16778.

Liu Y, Major AS, Zienkiewicz J, Gabriel CL, Veach RA, Moore DJ, et al. (2013) Nuclear transport modulation reduces hypercholesterolemia, atherosclerosis, and fatty liver. J Am Heart Assoc 2: e000093.

Lush CW, Cepinskas G, Sibbald WJ, Kvietys PR (2001) Endothelial E- and P-selectin expression in iNOS- deficient mice exposed to polymicrobial sepsis. Am J Physiol Gastrointest Liver Physiol 280: G291-297.

Opal SM (2010) New perspectives on immunomodulatory therapy for bacteraemia and sepsis. Int J Antimicrob Agents 36 Suppl 2: S70-73.

Qiu G, Wang C, Smith R, Harrison K, Yin K (2001) Role of IFN-gamma in bacterial containment in a model of intra-abdominal sepsis. Shock 16: 425-429.

Reddy RC, Chen GH, Newstead MW, Moore T, Zeng X, Tateda K, et al. (2001) Alveolar macrophage deactivation in murine septic peritonitis: role of interleukin 10. Infect Immun 69: 1394-1401.

Schroeder M, Brooks BD, Brooks AE (2017) The Complex Relationship between Virulence and Antibiotic Resistance. Genes (Basel) 8.

Steeber DA, Tang ML, Green NE, Zhang XQ, Sloane JE, Tedder TF (1999) Leukocyte entry into sites of inflammation requires overlapping interactions between the L-selectin and ICAM-1 pathways. J Immunol 163: 2176-2186.

Talcott B, Moore MS (1999) Getting across the nuclear pore complex. Trends Cell Biol 9: 312-318.

Torgerson TR, Colosia AD, Donahue JP, Lin YZ, Hawiger J (1998) Regulation of NF-kappa B, AP-1, NFAT, and STAT1 nuclear import in T lymphocytes by noninvasive delivery of peptide carrying the nuclear localization sequence of NF-kappa B p50. J Immunol 161: 6084-6092.

Veach RA, Liu D, Yao S, Chen Y, Liu XY, Downs S, et al. (2004) Receptor/transporter-independent targeting of functional peptides across the plasma membrane. J Biol Chem 279: 11425-11431.

Veach RA, Zienkiewicz J, Collins RD, Hawiger J (2012) Lethality in a murine model of pulmonary anthrax is reduced by combining nuclear transport modifier with antimicrobial therapy. PLoS One 7: e30527.

Vincent JL, Rello J, Marshall J, Silva E, Anzueto A, Martin CD, et al. (2009) International study of the prevalence and outcomes of infection in intensive care units. JAMA 302: 2323-2329.

Wallington J, Ning J, Titheradge MA (2008) The control of hepatic glycogen metabolism in an in vitro model of sepsis. Mol Cell Biochem 308: 183-192.

Weis K (2003) Regulating access to the genome. Nucleocytoplasmic transport throughout the cell cycle. Cell 112: 441-451.

Wolff SM (1973) Biological effects of bacterial endotoxins in man. J Infect Dis 128: Suppl:259-264.

Wynn JL, Scumpia PO, Delano MJ, O'Malley KA, Ungaro R, Abouhamze A, et al. (2007) Increased mortality and altered immunity in neonatal sepsis produced by generalized peritonitis. Shock 28: 675-683.

Wynn JL, Wilson CS, Hawiger J, Scumpia PO, Marshall AF, Liu JH, et al. (2016) Targeting IL-17A attenuates neonatal sepsis mortality induced by IL-18. Proc Natl Acad Sci U S A 113: E2627-2635.

(56) References Cited

OTHER PUBLICATIONS

Xiao W, Mindrinos MN, Seok J, Cuschieri J, Cuenca AG, Gao H, et al. (2011) A genomic storm in critically injured humans. J Exp Med 208: 2581-2590.

Ye X, Ding J, Zhou X, Chen G, Liu SF (2008) Divergent roles of endothelial NF-kappaB in multiple organ injury and bacterial clearance in mouse models of sepsis. J Exp Med 205: 1303-1315.

Zienkiewicz J, Armitage A, Hawiger J (2013) Targeting nuclear import shuttles, importins/karyopherins alpha by a peptide mimicking the NFkappaB1/p50 nuclear localization sequence. J Am Heart Assoc 2: e000386.

Zonneveld R, Martinelli R, Shapiro NI, Kuijpers TW, Plotz FB, Carman CV (2014) Soluble adhesion molecules as markers for sepsis and the potential pathophysiological discrepancy in neonates, children and adults. Crit Care 18: 204.

International Search Report and Written Opinion dated Oct. 16, 2018, from International Application No. PCT/US2018/037993, 11 pages.

\* cited by examiner

Figure 2:
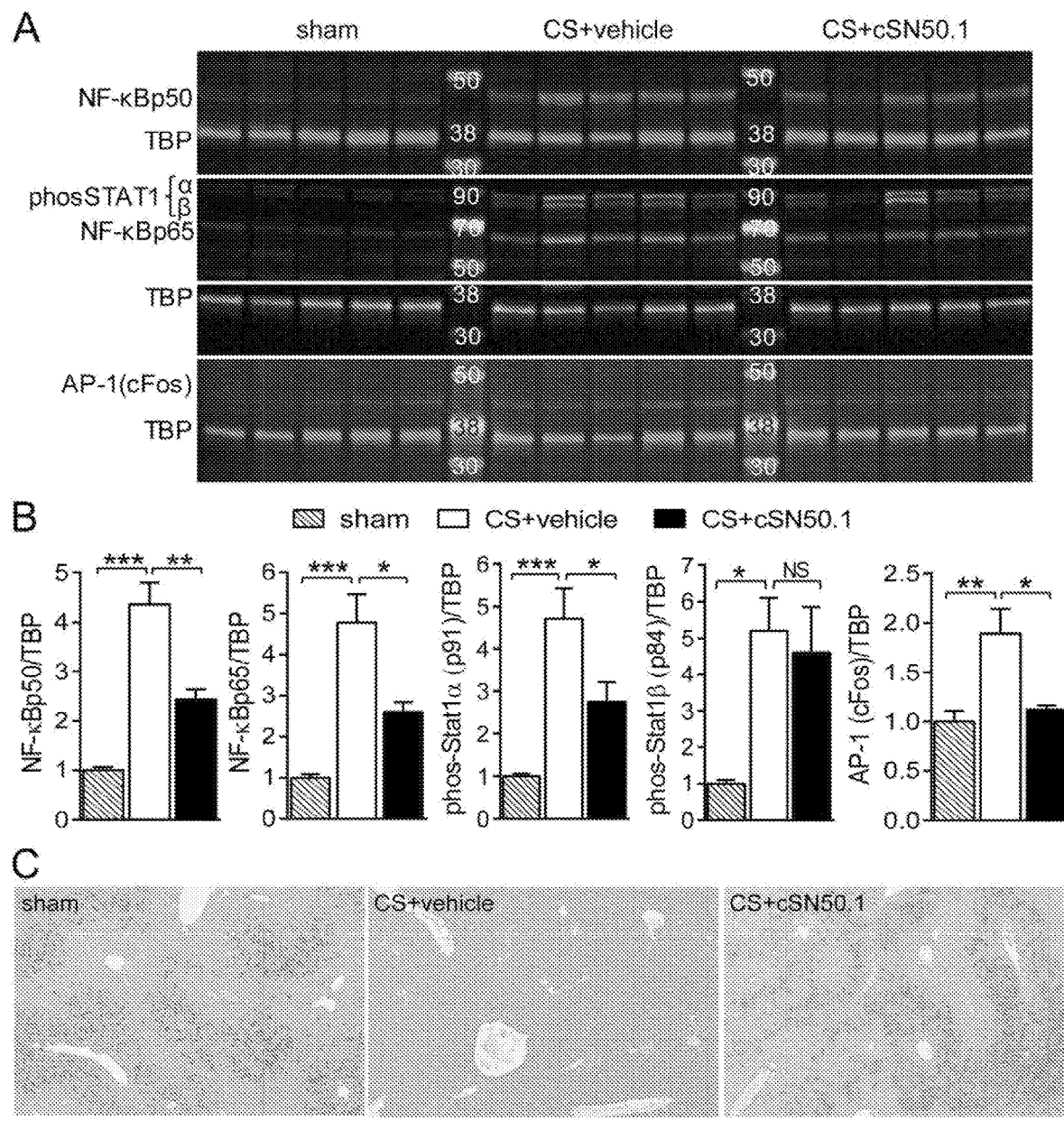

FIG. 2A, FIG. 2B, and FIG. 2C

FIG. 4A, FIG. 4B, FIG. 4C, and FIG. 4D

METHODS AND COMPOSITIONS FOR TREATING MICROBIAL INFLAMMATION

CROSS REFERENCE TO RELATED APPLICATIONS

This application is a national stage application filed under 35 U.S.C. § 371 of PCT/US2018/037993, filed Jun. 18, 2018, which claims the benefit of U.S. Provisional Patent Application No. 62/521,159, filed on Jun. 16, 2017, applications which are incorporated herein by reference in their entirety.

I. BACKGROUND

Microbial inflammation is the mechanism of systemic or localized infections due to bacterial, viral, fungal or protozoal pathogens. The end stage of some of these infections is sepsis defined as severe endothelial dysfunction syndrome in response to intravascular or extravascular infections causing reversible or irreversible injury to the microcirculation responsible for multiple organ failure. It represents one of the most challenging problems to prevent and treat in modern hospitals. Serious intravascular or extravascular infections culminate in severe microvascular endothelial injury that underlies hypotension and is difficult to reverse despite initiation of antimicrobial therapy and supportive measures. Microbial agents that escape defenses mounted by the innate and adaptive immune systems are not fully controlled by specific pathogen-directed antimicrobial therapy, which is often delayed. During their uncontrolled growth, especially in extravascular loci, bacteria reprogram their genomes through a quorum sensing mechanism and produce multiple virulence factors that potentiate microvascular injury. The host's innate immune responses are initiated and deranged by bacterial and fungal virulence factors and viral nucleic acids through the pattern recognition receptors, e.g. Toll-like receptors, present in immune cells and non-immune endothelial, fibroblasts and epithelial cells. Signals produced by these receptors are relayed to the cell's nucleus through activation of stress responsive transcription factors (SRTFs), such as nuclear factor kappa B (NF-κB), activator protein 1 (AP-1), nuclear factor of activated T-cells (NFAT), and signal transducer and activator of transcription 1 alpha (STAT-1α). Each of these transcription factors, either alone or in combination, triggers expression of multiple genes that encode proinflammatory cytokines and chemokines, as well as their receptors, signal transducers, and cell adhesion molecules, a response termed a genomic storm. The products of this genomic reprogramming mediate fever, microvascular endothelial instability responsible for low blood pressure, microvascular endothelial injury that underlies acute respiratory distress syndrome, disseminated intravascular coagulation, and multiple organ dysfunction, culminating in potentially lethal vascular collapse refractory to vasopressors and fluid resuscitation, a condition known as septic shock. Thus, reprograming of gene regulatory networks in response to a multitude of microbial insults is dependent on signaling to the host cell's nucleus comprising a fundamental process of microbial inflammation. Accordingly, in addition to pathogen-directed antimicrobial therapy new treatment methods and compositions are needed that can stop nuclear transport of the signal cascade and thereby inhibit the reprogramming of the host inflammatory response causing collateral damage to major organs such as lungs, kidneys, heart, brain, liver, skin and others.

II. SUMMARY

Disclosed are methods and compositions related to treating microbial inflammation and/or its end-stage form known as sepsis or septicemia.

In one aspect, disclosed herein are methods of treating/inhibiting/reducing microbial inflammation (such as, for example, acute inflammation, subacute inflammation, chronic inflammation, organ-specific inflammation, systemic inflammation, and/or sepsis) due to a microbial infection (such as, for example a viral, bacterial, fungal, or parasitic infection) in a subject comprising administering to the subject a therapeutically effective amount of an anti-microbial agent and a composition comprising one or more Nuclear Transport Modifier (NTM) such as, for example, an NTM that comprises the sequence set forth in SEQ ID NO: 1, SEQ ID NO: 2, SEQ ID NO: 3; SEQ ID NO: 4; SEQ ID NO: 5; SEQ ID NO: 6 or SEQ ID NO: 7, SEQ ID NO: 8, SEQ ID NO: 9, and/or SEQ ID NO: 16.

Also disclosed herein are methods of treating/inhibiting/reducing microbial inflammation (such as acute inflammation, subacute inflammation, chronic inflammation, organ-specific inflammation, systemic inflammation, and/or sepsis) associated thrombocytopenia in a subject comprising administering to the subject a therapeutically effective amount of a composition comprising one or more NTM.

In one aspect, disclosed herein are methods of reducing the microbial burden in the blood, brain, sinuses, upper respiratory tract, or lungs, heart, bone marrow, spleen, liver, kidneys, urinary tract, bladder, aural cavities, stomach, intestines, skin, eyes, teeth or gingiva, comprising administering to the subject a therapeutically effective amount of a composition comprising one or more NTM.

Also disclosed herein are methods of any preceding aspect, wherein the composition comprising the NTM does not comprise the anti-microbial agent.

In one aspect, disclosed herein are methods of any preceding aspect, wherein the composition comprising the NTM does comprise the anti-microbial agent.

Also disclosed herein are methods of reducing levels of a Stress Responsive Transcription Factor (SRTF) in a cell (such as, a monocyte, macrophage, dendritic cell, innate lymphoid cell, B cell, NK cell, NK T cell, T cell, endothelial cell, or epithelial cell) at a site of inflammation in a subject with an infection, comprising administering to the subject a therapeutically effective amount of a composition comprising one or more Nuclear Transport Modifiers (NTMs) such as, for example, an NTM that comprises the sequence set forth in SEQ ID NO: 1, SEQ ID NO: 2, SEQ ID NO: 3; SEQ ID NO: 4; SEQ ID NO: 5; SEQ ID NO: 6 or SEQ ID NO: 7, SEQ ID NO: 8, SEQ ID NO: 9, and/or SEQ ID NO: 16.

Also disclosed are methods of reducing levels of a SRTF of any preceding aspect, wherein the SRTF comprises NF-κB (such as, NF-κB is NF-κB 1, NF-κB Rel A or a combination thereof), STAT1α, and/or AP-1.

Also disclosed are methods of reducing levels of a Sterol Regulatory Element Binding Proteins (SREBPs) wherein SREBP comprises SREBP1a, SREBP1c, SREBP2.

In one aspect, disclosed herein are methods of increasing the therapeutic efficacy of an anti-microbial in a subject comprising administering to the subject an NTM comprising the sequence set forth in SEQ ID NO: 1, SEQ ID NO: 2, SEQ ID NO: 3; SEQ ID NO: 4; SEQ ID NO: 5; SEQ ID NO: 6 or SEQ ID NO: 7, SEQ ID NO: 8, SEQ ID NO: 9, or SEQ ID NO: 16.

III. BRIEF DESCRIPTION OF THE DRAWINGS

The accompanying drawings, which are incorporated in and constitute a part of this specification, illustrate several embodiments and together with the description illustrate the disclosed compositions and methods.

FIG. 1 presents a schematic showing that nuclear transport is a pivotal checkpoint in genomic regulation of microbial inflammation. Legend: TLRs (Toll-like receptors); Ca2+ (calcium ions); IL-1R and IL-18R (interleukin 1 and 18 receptors, respectively); IFN-γ (Interferon-gamma); IFNGR (Interferon-gamma receptor); SFKs (Src family of protein tyrosine kinases); MyD88 (Myeloid Differentiation Primary Response 88); IRAK (interleukin-1 receptor-associated kinase); JAK (Janus kinase); P (Phosphate group); Ub (Ubiquitin); CaM (Calmodulin); TRAF6 (TNF receptor-associated factor 6); IKK (I kappa B kinase); IκBα (NF-κB inhibitor alpha); JNK (c-Jun N-terminal kinase); MAPKs (mitogen-activated protein kinases); NFAT (nuclear factor of activated T cells); AP-1 (Activator protein 1); NF-κB (Nuclear factor kappa B); NPC (nuclear pore complex); STAT1 (signal transducer and activator of transcription 1); Imp α5 (Importin alpha 5); Imp β1 (Importin beta 1); TNFα (tumor necrosis factor alpha); IL-1, IL-6, IL-10 and IL-17 (interleukin 1, 6, 10 and 17, respectively); MCP-1 (Monocyte Chemoattractant Protein-1).

FIGS. 2A, 2B, and 2C show that nuclear transport of SRTFs is reduced and normal liver architecture is protected in infected mice treated with NTM. FIG. 2A shows that nuclear content of NF-κBp50, NF-κBp65, pY701 phospho-STAT1α (MW 91) and -STAT1β (MW 84), and AP-1 (cFos) in livers collected 12 h after infection from sham-infected or cecal slurry (CS)-infected mice treated with NTM (cSN50.1) or vehicle. CS that comprised freshly isolated gut microbiome from a donor animal was standardized before intraperitoneal injection to cause polymicrobial peritonitis and sepsis. Each lane is the nuclear extract from one mouse; lanes shown in each row are from the same gel. Immunoblots shown are representative of 2 independent nuclear extract preparations. FIG. 2B shows quantitative analysis of immunoblots shown in 2A. All samples were normalized to TATA binding protein (TBP) on the same immunoblot (Data points are displayed as mean+SEM of fold change, n=10/group; *p<0.05, p<0.005, *p<0.0001 by t test, NS=not significant). FIG. 2C shows liver sections collected 12 h after infection from sham-infected or CS-infected mice treated with NTM (cSN50.1) or vehicle stained with PAS. Images are representative of 5 mice/group.

Figure 3:
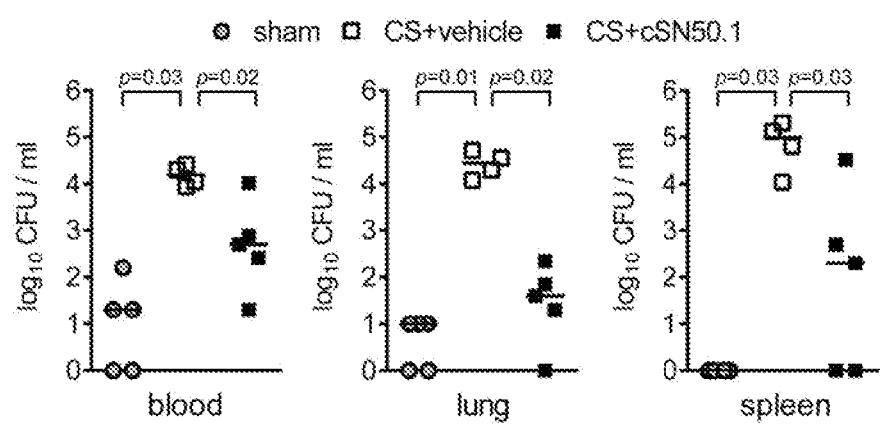

FIG. 3 shows that bacterial clearance is improved in infected mice treated with NTM. Bacterial Colony-Forming Units (CFU) were determined by serial dilution of whole blood and organ homogenates collected 12 h after infection from sham- or CS-infected mice treated with NTM (cSN50.1) or vehicle and cultured under standard conditions. Bars represent median values from 4-5 mice/group (p values determined by Mann-Whitney test).

Figure 4:
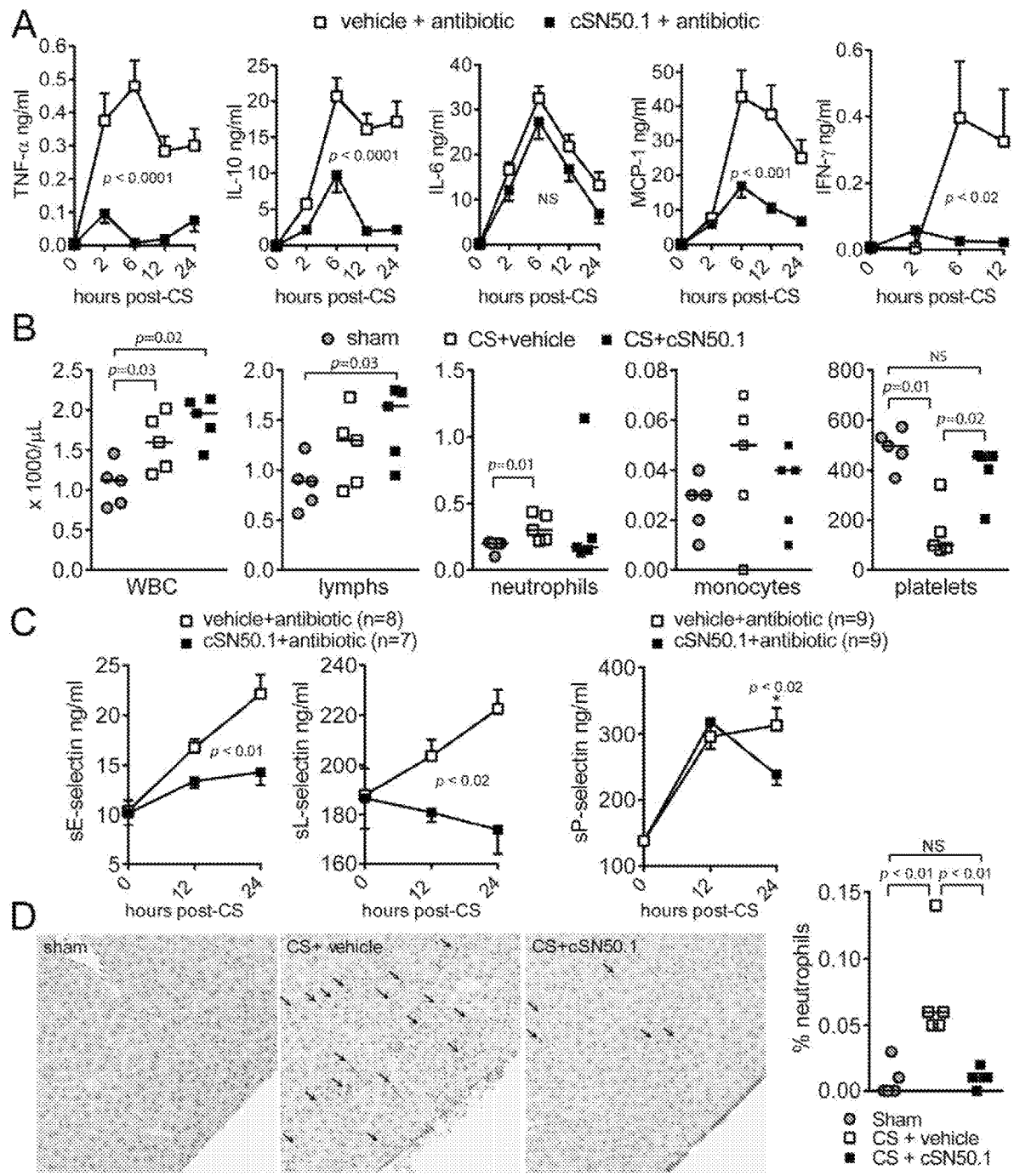

FIGS. 4A, 4B, 4C, and 4D shows that NTM modulates blood and vascular responses to sepsis. FIG. 4A shows cytokines/chemokine measured in blood plasma by cytometric bead array before and at 2 h, 6 h, 12 h, and 24 h after CS infection. Antibiotic therapy with meropenem began at 12 h post-infection. (n=20 mice/group; p values calculated by two-way repeated measures ANOVA). IFN-γ measured by ELISA in blood plasma before and at 2 h, 6 h and 12 h after CS infection. (vehicle+antibiotic, n=8; cSN50.1+antibiotic, n=13; p values calculated by two-way repeated measures ANOVA). FIG. 4B shows the total WBC, lymphocytes, neutrophils, monocytes, and platelets in whole blood collected 12 h after infection from sham-infected or CS-infected mice treated with NTM (cSN50.1) or vehicle. Bars represent median values from 5 mice/group (p values determined by Mann-Whitney test). FIG. 4C shows soluble E-selectin, L-selectin, and P-selectin measured in blood plasma before and at 12 h and 24 h after CS infection. Antibiotic therapy with meropenem began at 12 h post-infection. (p values for sE-selectin and sL-selectin calculated by two-way repeated measures ANOVA, p value for sP-selectin determined by Mann-Whitney test at 24 h only, n=9/group). FIG. 4D shows representative images (400× magnification) and quantification of neutrophils (indicated by arrows) in the hepatic parenchyma of livers collected 12 h after infection from sham-infected or CS-infected mice treated with NTM (cSN50.1) or vehicle. The percentage of positive brown (DAB-positive) stained cells was calculated as a total analyzed number of positive cells divided by total number cells in the section of liver. Bars represent median values from 5 mice/group (p values determined by Mann-Whitney test).

Figure 5:
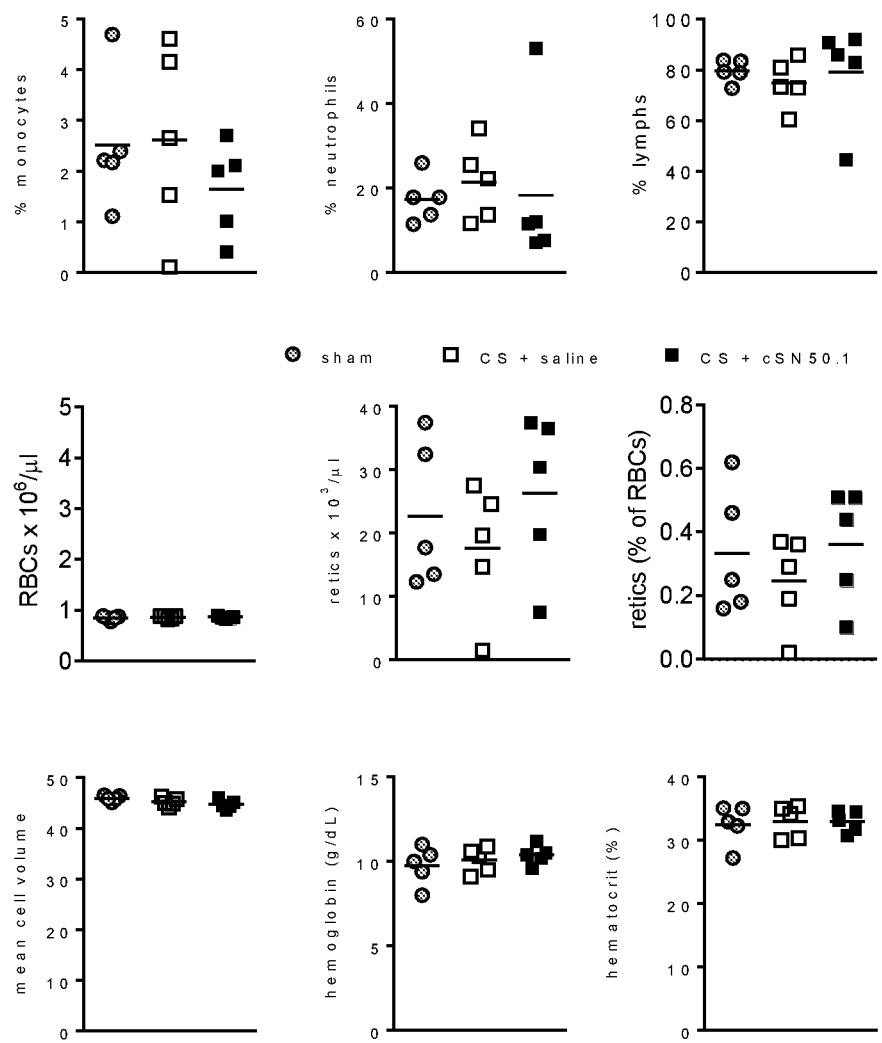

FIG. 5 shows the parameters of the Complete Blood Count (CBC) shown in FIG. 4B that are not changed by infection or NTM treatment (N=5 mice/group). Bars represent mean values from 5 mice/group. No significant differences were determined by Maim-Whitney test.

Figure 6:
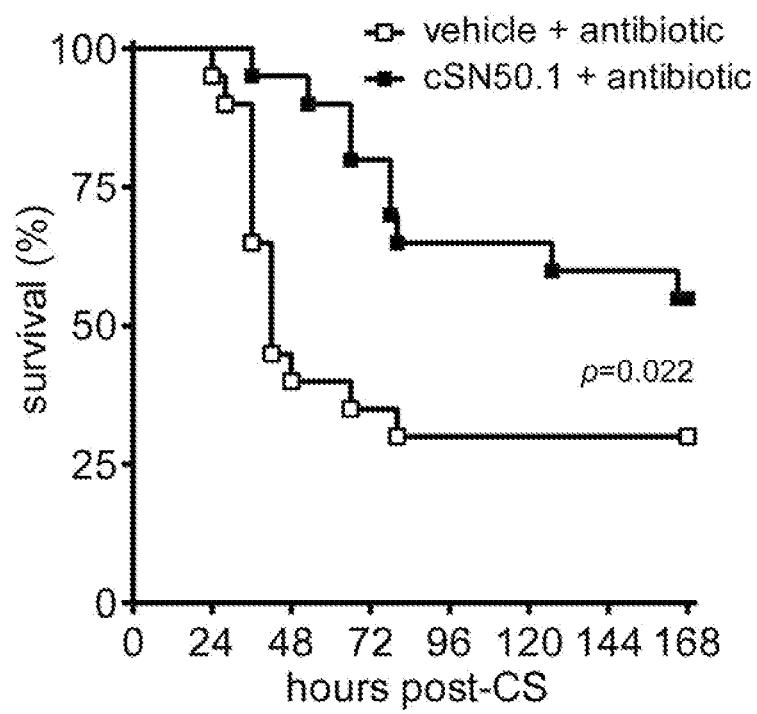

FIG. 6 shows that survival is increased by combining NTM treatment with antibiotic therapy. Mice were infected with CS and treated with vehicle or NTM (cSN50.1), both supplemented by antibiotic therapy with meropenem (n=20 mice/group; Kaplan-Meier survival plot with p value calculated by log rank analysis).

IV. DETAILED DESCRIPTION

Before the present compounds, compositions, articles, devices, and/or methods are disclosed and described, it is to be understood that they are not limited to specific synthetic methods or specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

A. Definitions

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

The terms "patient," "subject" and "individual" are used interchangeably herein, and mean an animal (e.g., mammalian (such as human, equine, bovine, ovine, porcine, canine, etc.), reptilian, piscine, etc.) to be treated, diagnosed and/or to obtain a biological sample from.

As used herein, "bind," "binds," or "interacts with" means that one molecule recognizes and adheres to a particular second molecule in a sample or organism, but does not substantially recognize or adhere to other structurally unrelated molecules in the sample. Generally, a first molecule that "specifically binds" a second molecule has a binding affinity greater than about $10^8$ to $10^{12}$ moles/liter for that second molecule and involves precise "hand-in-a-glove" docking interactions that can be covalent and non-covalent (hydrogen bonding, hydrophobic, ionic, and van der Waals).

By the phrase "nuclear transport modifier" and "NTM" is meant a peptide that is capable of modulating entry of transcription factors into the nucleus. An example of a nuclear transport modifier is a 26-29 amino acid peptide derived from human nuclear factor kappa B1 nuclear localization sequence and from human Fibroblast Growth Factor 4 signal sequence hydrophobic region. This phrase is used interchangeably with the phrase "nuclear import inhibitor."

In an NTM as described herein, any of the amino acid residues in the NTM sequence can be mutated and/or modified (i.e., to form mimetics) so long as the modifications do not affect the translocation-mediating function of the peptide. Thus, the word "peptide" includes mimetics and the word "amino acid" includes modified amino acids, unusual amino acids, D-form amino acids, etc.

As used herein, the phrases "nuclear import adaptor" and "nuclear transport adaptor" mean a cell component capable of mediating transport of a protein usually larger than 45 kD (e.g., a transcription factor) into the nucleus. An example of a nuclear transport adaptor is an importin also known as karyopherin.

As used herein, "protein" and "polypeptide" are used synonymously to mean any peptide-linked chain of amino acids, regardless of length or post-translational modification, e.g., glycosylation or phosphorylation.

By the term "gene" is meant a nucleic acid molecule that codes for a particular protein, or in certain cases, a functional or structural RNA molecule.

As used herein, a "nucleic acid" or a "nucleic acid molecule" means a chain of two or more nucleotides such as RNA (ribonucleic acid) and DNA (deoxyribonucleic acid).

The term "labeled," with regard to a nucleic acid, protein, probe or antibody, is intended to encompass direct labeling of the nucleic acid, protein, probe or antibody by coupling (i.e., physically or chemically linking) a detectable substance (detectable agent) to the nucleic acid, protein, probe or antibody.

As used herein, the terms "therapeutic," and "therapeutic agent" are used interchangeably, and are meant to encompass any molecule, chemical entity, composition, drug, cell(s), therapeutic agent, chemotherapeutic agent, or biological agent capable of preventing, ameliorating, or treating a disease or other medical condition. The term includes small molecule compounds, antisense reagents, siRNA reagents, antibodies, enzymes, peptides organic or inorganic molecules, cells, natural or synthetic compounds and the like.

As used herein, the term "treatment" is defined as the application or administration of a therapeutic agent to a patient or subject, or application or administration of the therapeutic agent to an isolated tissue or cell line from a patient or subject, who has a disease, a symptom of disease or a predisposition toward a disease, with the purpose to cure, heal, alleviate, relieve, alter, remedy, ameliorate, improve or affect the disease, the symptoms of disease, or the predisposition toward disease.

A "decrease" can refer to any change that results in a smaller amount of a symptom, disease, composition, condition, or activity. A substance is also understood to decrease the genetic output of a gene when the genetic output of the gene product with the substance is less relative to the output of the gene product without the substance. Also for example, a decrease can be a change in the symptoms of a disorder such that the symptoms are less than previously observed. A decrease can be any individual, median, or average decrease in a condition, symptom, activity, composition in a statistically significant amount. Thus, the decrease can be a 1, 2, 3, 4, 5, 6, 7, 8, 9, 10, 15, 20, 25, 30, 35, 40, 45, 50, 55, 60, 65, 70, 75, 80, 85, 90, 95, or 100% decrease so long as the decrease is statistically significant.

"Inhibit," "inhibiting," and "inhibition" mean to decrease an activity, response, condition, disease, or other biological parameter. This can include but is not limited to the complete ablation of the activity, response, condition, or disease. This may also include, for example, a 10% reduction in the activity, response, condition, or disease as compared to the native or control level. Thus, the reduction can be a 10, 20, 30, 40, 50, 60, 70, 80, 90, 100%, or any amount of reduction in between as compared to native or control levels.

An "increase" can refer to any change that results in a greater amount of a symptom, disease, composition, condition or activity. An increase can be any individual, median, or average increase in a condition, symptom, activity, composition in a statistically significant amount. Thus, the increase can be a 1, 2, 3, 4, 5, 6, 7, 8, 9, 10, 15, 20, 25, 30, 35, 40, 45, 50, 55, 60, 65, 70, 75, 80, 85, 90, 95, or 100% increase so long as the increase is statistically significant.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular nuclear transport modifier (NTM) is disclosed and discussed and a number of modifications that can be made to a number of molecules including the NTM are discussed, specifically contemplated is each and every combination and permutation of NTM and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

B. Methods of Use

Although compositions, kits, cells, and methods similar or equivalent to those described herein can be used in the practice or testing of the present invention, suitable compositions, kits, cells, and methods are described below. All publications, patent applications, and patents mentioned herein are incorporated by reference in their entirety. U.S. patent application Ser. No. 14/349,918, and U.S. Pat. No. 7,553,929, for example, are incorporated by reference in their entireties. In the case of conflict, the present specification, including definitions, will control. The particular embodiments discussed below are illustrative only and not intended to be limiting.

In response to infection with a microbe such as, for example, a virus, bacterium, fungus, or parasite the host immune system attempts to eliminate the infecting microbe by employing arms of the innate and adaptive immune systems including the secretion of cytokines, antibodies, and effector mechanisms of granulocyte, monocyte, macrophage, dendritic cell, innate lymphoid cell, NK cells, NK T cells, T cells, B cells, and plasma cells. In any inflammation, inflammatory signaling cascades initiated by cell responses to microbial virulence factors and cytokines culminate in nuclear translocation of stress-responsive transcription factors (SRTFs) that upregulate inflammatory gene networks. Unchecked, this genomic reprogramming (genomic storm) leads to endothelial dysfunction, multi-organ failure and ultimately fatal shock, known as septic shock, that represents the ultimate end stage of microbial inflammation, one of the 10 leading causes of death in developed and developing countries.

During an infection, production of toxic cytokines depends on tightly-regulated intracellular signal transduction by SRTFs, such as NF-κB, AP-1, NF-AT, STAT-1, and others. NF-κB is the paradigmatic SRTF and has a role in microbial inflammation pathogenesis with crucial roles played at the levels of myeloid, lymphoid, endothelial, and epithelial cells. However, other SRTFs, including NF-AT, AP-1, and STAT-1, have also been involved by activating numerous target genes that encode mediators of inflammation and apoptosis, which underlie destruction of target tissues. Moreover, metabolic transcription factors such as Sterol-Regulatory Element Binding Proteins (SREBPs) 1a, 1c, and 2 can be activated by certain microbial agents. These positive effectors of pro-inflammatory immune signaling to the nucleus participate in an auto-stimulatory loop, which amplifies the inflammatory process initiated by microbial triggers. To carry out these functions, activated SRTFs and SREBPs are ferried to the nucleus of cells responding to innate and adaptive immune stimulation. Thus, uncontrolled nuclear translocation of SRTFs and SREBPs represents an additional feature of microbial inflammation and its end-stage, sepsis.

Small transcription factors (<50 kD), usually those regulating the housekeeping genes that encode cell survival factors, have free passage from the cytoplasm to the nucleus. In contrast, nuclear transport of transcription factors larger than 50 kD, such as SRTFs, is guided by one or more nuclear localization sequences (NLSs). These intracellular "zip codes" are displayed on SRTFs upon stimulation of immune and non-immune cells by microbial insults. NLSs are then recognized by nuclear transport adaptor proteins, importins/karyopherins alpha (Imp α) (see FIG. 1). The stimulus-induced formation of SRTF and importins α complexes also encompasses importin beta 1 (Imp β1), which is recognized by nuclear pore proteins to allow translocation of the cargo to the nucleus. Until recently, nuclear transport has been targeted through the forced expression of genes that encode inhibitors of proinflammatory SRTFs, such as the degradation-resistant inhibitor of NF-κB termed IκBα. However, NF-κB is only one of multiple SRTFs that mediate signaling to the nucleus in response to infection. Other SRTFs, such as AP-1, STAT1 and NFAT, are also transported to the nucleus during the inflammatory response yet their nuclear transport is not impeded by IκBα; contrarily, the AP-1 pathway is activated. Targeting nuclear transport, a pivotal checkpoint integrating translocation of multiple transcription factors to the nucleus, can be a more efficient strategy than targeting signaling pathways of individual transcription factors. This concept was proven by design and development of Nuclear Transport Modifiers (NTMs).

NTMs target the nuclear transport shuttles, Imp α5 and Imp β1, that translocate SRTFs to the nucleus and control signal transduction pathways, which culminate in genomic reprogramming. In recent preclinical studies, a highly soluble cell-penetrating NTM (cSN50.1), with dual specificity was used. This NTM has segments that bind both Imp α5, which recognizes NLS derived from NFκB1, and Imp β1, which recognizes the signal-sequence hydrophobic region (SSHR) derived from Fibroblast Growth Factor 4. SSHR also serves as a membrane translocating motif (MTM) to enable intracellular delivery of peptides and proteins through an ATP- and endocytosis-independent mechanism. This and other NTMs have been shown to inhibit nuclear translocation of SRTFs and metabolic transcription factors, Sterol Regulatory Element Binding Proteins (SREBPs) thereby reducing inflammatory responses, microvascular injury, apoptosis and hemorrhagic necrosis as well as metabolic derangements with a concomitant gain in survival, in models of lethal shock induced by bacterial toxins.

A novel form of immunotherapy that targets nuclear import as described herein can arrest inflammation-driven destruction of microbe-infected tissue and surrounding area of a given organ. With respect to microbial inflammation (such as, for example, acute inflammation, subacute inflammation, chronic inflammation, organ-specific inflammation, systemic inflammation, and/or sepsis), pro-inflammatory signaling initiated through stimulation of the principal receptors of innate immunity, Toll-like receptors (TLRs), is one mechanism that activates antigen-presenting cells (APCs). Inhibiting nuclear transport at a common "checkpoint" located downstream of TLRs and cytokine receptors globally suppresses expression of inflammatory genes thereby calming the genomic storm and averting multiple organ injury. Reprograming of gene regulatory networks in response to a multitude of microbial insults is dependent on signaling to the host cell's nucleus comprising a fundamental process of microbial inflammation (see FIG. 1 for a depiction).

Accordingly, in one aspect, disclosed herein are methods of reducing levels of a Stress Responsive Transcription Factor (SRTF) and metabolic transcription factors, Sterol Regulatory Element Binding Proteins (SREBPs) in a cell's nucleus at a site of inflammation in a subject with an infection, comprising administering to the subject a therapeutically effective amount of a composition comprising one or more Nuclear Transport Modifiers (NTMs).

It is understood and herein contemplated that by reducing the levels of SRTF and metabolic transcription factors, Sterol Regulatory Element Binding Proteins (SREBPs), in a cell's nucleus, the disclosed NTM can reduce, inhibit, and/or prevent microbial inflammation causing genomic storm (such as, for example, acute inflammation, subacute inflammation, chronic inflammation, organ-specific inflammation, systemic inflammation, and/or sepsis), and consequently the occurrence of endothelial dysfunction, multi-organ failure and ultimately fatal shock associated with sepsis. Accordingly, described herein is a method of treating, inhibiting, reducing, and/or preventing microbial inflammation (such as, for example, acute inflammation, subacute inflammation, chronic inflammation, organ-specific inflammation, systemic inflammation, and/or sepsis) comprising administering to the subject with the microbial inflammation a composition comprising NTM in combination with one or more anti-microbial agents.

In one aspect, the method for reducing levels of SRTF and SREBPs (such as, for example, SREBP1a, SREBP1c, SREBP2) in a cell, methods treating, inhibiting, reducing, and/or preventing microbial inflammation (such as, for example, acute inflammation, subacute inflammation, chronic inflammation, organ-specific inflammation, systemic inflammation, and/or sepsis), and methods of clearing a microbe from host tissues include administering a therapeutically effective amount of a composition comprising one or more nuclear transport modifier (NTM) to the mammalian subject. Administration of the composition decreases microbial inflammation by attenuating expression of at least one stress-responsive transcription factor-regulated gene and or at least one Sterol-Regulatory Element Binding Proteins (SREBPs)-regulated gene. Thus, the effective dose is an amount effective for reducing importin alpha-mediated nuclear translocation of at least one stress response stress responsive transcription factors (SRTF) and reducing inflammation caused by infection in the mammalian subject. Similarly, the effective dose is an amount effective for reducing importin beta-mediated nuclear translocation of at least one metabolic transcription factors, Sterol-Regulatory Element Binding Protein (SREBP) and reducing inflammation caused by infection in the mammalian subject. The NTM may bind to importin alpha, to importin beta, or to both importin alpha and importin beta.

An important aspect of the Nuclear Transport Modifier exemplified by cSN50.1 peptide and its congeners is their ability to reach the site of infection and the infected host cell, as well as other myeloid, lymphoid, and non-lymphoid organs. The mechanism of intracellular delivery of this peptide has been elucidated and an endocytosis-independent process of crossing the plasma membrane mediated by the membrane-translocating motif (MTM), which is based on the signal sequence hydrophobic region (SSHR) derived from Kaposi FGF, has been documented (Veach et al. (2004) J Biol Chem 279: 11425-11431). The amphipathic helix-based structure of SSHR facilitates its insertion directly into the plasma membrane and the tilted transmembrane orientation permits the translocation of the Nuclear Transport Modifier through the phospholipid bilayer of the plasma membrane directly to the interior of the cell without perturbing membrane integrity. This mechanism explains the efficient delivery of SSHR-guided cargo across the plasma membrane of multiple cell types involved in microbial inflammation.

The NTMs disclosed herein are derived from N50-containing NTMs (SN50, cSN50, and cSN50.1) that are comprised of a hydrophilic N50 motif patterned on the nuclear localization sequence (NLS) region of the NFκB1/p50 subunit (see Table 1) fused to a motif from the signal sequence hydrophobic region (SSHR) of human fibroblast growth factor 4. The SSHR allows peptides to cross the plasma membrane by an ATP- and endosome-independent mechanism, and the N50 motif was designed to bind to importins α during stimulus-initiated signaling and thereby limit docking of NLS-bearing SRTFs to their adaptor proteins and reduce nuclear import of activated STRFs.

TABLE 1

Amino Acid Sequences of Peptides Used

| NTM | SSHR | NLS | SEQ ID NO: |
|---|---|---|---|
| N50 | | VQRKRQKLMP | 10 |
| N50M | | VQRDEQKLMP | 11 |
| cN50.1 | | CVQRKRQKLMPC | 12 |
| SN50 | AAVALLPAVLLALLAP | VQRKRQKLMP | 13 |
| SSHR-1 | AAVALLP | | 14 |
| SSHR-2 | AVLLALLAP | | 15 |

N50-sequence derived from the NLS region of NFκB1/p50; N50M-sequence of control peptide with KR to DE mutation (bolded); cN50.1-sequence of cyclized version of N50 just as cSN50.1 is a cyclized version of SN50. Hydrophobic regions of the SSHR domain are distinguished from the cluster of basic amino acids (NLS). NTM indicates nuclear transport modifier; SSHR, signal sequence hydrophobic region; NLS, nuclear localization sequence.

SN50 is a fragment linked peptide combining the signal sequence hydrophobic region (SSHR) of the Kaposi fibroblast growth factor (K-FGF) and the nuclear localization signal (NLS) of the p50 subunit of NFκB1. Any mimetics, derivatives, or homologs of SN50 may be used in the compositions, methods, and kits disclosed herein. The sequence of SN50 is AAVALLPAVLLAL-LAPVQRKRQKLMP (SEQ ID NO: 13). Generation and use of SN50 is described in U.S. Pat. No. 7,553,929.

cSN50 is a fragment-designed cyclic peptide combining the hydrophobic region of the Kaposi fibroblast growth factor signal sequence with the nuclear localization signal (NLS) of the p50-NFKB1 and inserting a cysteine on each side of the NLS to form an intrachain disulfide bond. The amino acid sequence of cSN50 is AAVALLPAVLLAL-LAPCYVQRKRQKLMPC (SEQ ID NO: 1). Methods of making and using cSN50 are described, for example, in U.S. Pat. Nos. 7,553,929 and 6,495,518. These patents are incorporated herein by reference in their entireties.

In another embodiment, cSN50.1 may be administered to protect cells, tissues, or organs from immune destruction. cSN50.1 is a cyclic peptide having the sequence of cSN50 with the exception that the tyrosine at position 18 of cSN50, adjacent to the first cysteine, has been removed. The amino acid sequence of cSN50.1 is AAVALLPAVLLAL-LAPCVQRKRQKLMPC (SEQ ID NO: 2). cSN50.1 was designed to increase the solubility of the cSN50 peptide; i.e., a tyrosine was removed from the sequence of cSN50 to increase solubility. cSN50 is soluble at levels of ranging from 2.0 mg/mL to 40 mg/mL depending on the method of synthesis and purification whereas cSN50.1 is soluble at levels of at least 100 mg/ml. cSN50.1 is also encompassed by SEQ ID NO: 3, SEQ ID NO: 4 and SEQ ID NO: 5: Additional examples of NTMs include fragment-designed and synthesized peptides in which cargo is incorporated as two, rather than one, modules or cargos derived from intracellular proteins other than NFκB 1. Such additional examples include the sequences of SEQ ID NO: 6, SEQ ID NO: 7, SEQ ID NO: 8, and SEQ ID NO: 9.

Accordingly, the Nuclear Transport Modifier (NTM) for use in the disclosed methods of treating, inhibiting, reducing, and/or preventing microbial inflammation (such as, for example, acute inflammation, subacute inflammation, chronic inflammation, organ-specific inflammation, systemic inflammation, and/or sepsis) may be, for example, an NTM having the sequence Xaa Xaa Xaa Xaa Leu Leu Pro Xaa Xaa Leu Leu Ala Leu Leu Ala Pro Xaa Xaa Xaa Gln Arg Lys Arg Gln Lys Xaa Xaa Xaa Xaa (SEQ ID NO: 3), wherein Xaa is any amino acid or is absent. For example, the Nuclear Transport Modifier can have the sequence Xaa Xaa Xaa Xaa Leu Leu Pro Xaa Xaa Leu Leu Ala Leu Leu Ala Pro Cys Xaa Xaa Gln Arg Lys Arg Gln Lys Xaa Xaa Xaa Cys, where Xaa is any amino acid or is absent (SEQ ID NO: 4). As another example, the Nuclear Transport Modifier can have the sequence Xaa Xaa Xaa Xaa Leu Leu Pro Xaa Xaa Leu Leu Ala Leu Leu Ala Pro Cys Xaa Gln Arg Lys Arg Gln Lys Xaa Xaa Xaa Cys, where Xaa is any amino acid or is absent (SEQ ID NO: 5). In one embodiment, the Nuclear Transport Modifier is cSN50.1 having the sequence set forth in SEQ ID NO: 2. In another example of an NTM, the NTM has the sequence Xaa Xaa Xaa Xaa Leu Leu Pro Xaa Xaa Leu Leu Ala Val Leu Ala Pro Xaa Xaa Xaa Gln Arg Lys Arg Gln Lys Xaa Xaa Xaa Xaa Xaa, where Xaa is any amino acid or is absent (SEQ ID NO: 6). In yet another example, the NTM has the sequence Ala Ala Val Ala Leu Leu Pro Ala Val Leu Leu Ala Val Leu Ala Pro Cys Val Gln Arg Lys Arg Gln Lys Leu Met Pro Cys (SEQ ID NO: 7). In a further example, the NTM has the sequence Xaa Xaa Xaa Xaa Leu Leu Pro Xaa Xaa Leu Leu Ala Val Leu Ala Pro Xaa Xaa Xaa Gln Arg Asp Glu Gln Lys Xaa Xaa Xaa Xaa Xaa, where Xaa is any amino acid or is absent (SEQ ID NO: 8). In another example, the NTM has the sequence Ala Ala Val Ala Leu Leu Pro Ala Val Leu Leu Ala Val Leu Ala Pro Cys Val Gln Arg Asp Glu Gln Lys Leu Met Pro Cys (SEQ ID NO: 9). In one aspect disclosed herein are methods of treating, inhibiting, reducing, and/or preventing microbial inflammation (such as, for example, acute inflammation, subacute inflammation, chronic inflammation, organ-specific inflammation, systemic inflammation, and/or sepsis) in a subject comprising administering to the subject an anti-microbial agent and a composition comprising one or more NTMs including, but not limited to SN50 having the sequence set forth in SEQ ID NO: 1 or cSN50.1 having the sequence set forth in SEQ ID NO: 2, cSN50.1 beta having the sequence set forth in SEQ ID NO: 16, or any of the NTMs disclosed herein having the amino acid sequence set forth in SEQ ID NO: 3, SEQ ID NO: 4, SEQ ID NO: 5, SEQ ID NO: 6, SEQ ID NO: 7, SEQ ID NO: 8, or SEQ ID NO: 9. In one aspect the NTM can be cSN50.1 beta comprising the amino acid sequence AAVALLPAVL-LALLAPCVQRDEQKLMPC (SEQ ID NO:16). cSN50.1 beta is a cyclized peptide having the sequence of cSN50.1 with the exception that the lysine at the position 21 has been replaced by aspartic acid and the arginine residue at the position of 22 has been replaced by glutamic acid.

As noted above, the methods disclosed herein can be used in treating, inhibiting, reducing, and/or preventing microbial inflammation (such as, for example, acute inflammation, subacute inflammation, chronic inflammation, organ-specific inflammation, systemic inflammation, and/or sepsis). In one aspect, disclosed herein are methods of treating, inhibiting, reducing, and/or preventing microbial inflammation (such as, for example, acute inflammation, subacute inflammation, chronic inflammation, organ-specific inflammation, systemic inflammation, and/or sepsis) in a subject comprising administering to a subject a therapeutically effective amount of an anti-microbial agent and a composition comprising one or more NTM (such as, for example, SEQ ID NO: 1, SEQ ID NO: 2, SEQ ID NO: 3; SEQ ID NO: 4; SEQ ID NO: 5; SEQ ID NO: 6 or SEQ ID NO: 7, SEQ ID NO: 8, SEQ ID NO: 9, or SEQ ID NO: 16).

It is understood and herein contemplated that one of the deleterious effects of microbial inflammation (such as, for example, acute inflammation, subacute inflammation, chronic inflammation, organ-specific inflammation, systemic inflammation, and/or sepsis) can be the occurrence of a loss of platelets (i.e., thrombocytopenia) in the subject with the microbial inflammation. As a result of inflammation (such as, for example, acute inflammation, subacute inflammation, chronic inflammation, organ-specific inflammation, systemic inflammation, and/or sepsis), many pro- and anti-inflammatory cytokines are released resulting in the microvascular endothelial injury that evokes activation and deposition of blood platelets thereby resulting in their "consumption" manifested by a decreased platelet count in the blood (thrombocytopenia). This process is accompanied by generation of clotting enzyme, thrombin, but also results in production of plasminogen activator that leads to formation of fibrinolytic enzyme, plasmin. Thus, fibrinogen can be depleted and both uncontrolled thrombi formation and bleeding may occur while circulating platelets are depleted, a process known as thrombocytopenia without or with Disseminated Intravascular Coagulation. Typical platelet counts for adults is between 150,000 and 400,000/µL but these numbers can be less 80,000/µL due to microbial inflammation. In one aspect, it is understood that by treating the microvascular endothelial dysfunction in the subject displaying the microbial inflammation, the thrombocytopenia is ameliorated. Therefore, disclosed herein are methods of treating/inhibiting/reducing thrombocytopenia associated with inflammation (such as, for example, acute inflammation, subacute inflammation, chronic inflammation, organ-specific inflammation, systemic inflammation, and/or sepsis) in a subject comprising administering to the subject a therapeutically effective amount of a composition comprising one or more NTM (such as, for example, SEQ ID NO: 1, SEQ ID NO: 2, SEQ ID NO: 3; SEQ ID NO: 4; SEQ ID NO: 5; SEQ ID NO: 6 or SEQ ID NO: 7, SEQ ID NO: 8, SEQ ID NO: 9, or SEQ ID NO: 16). It is understood and herein contemplated that the disclosed methods of treating, inhibiting, or reducing thrombocytopenia can further comprise the addition of an anti-microbial agent and/or an anti-inflammatory agent.

It is also understood and herein contemplated that proinflammatory signaling to the nucleus has also been implicated in rapid glycogen depletion in the liver during microbial inflammation. However, as shown herein, NTM treatment prevented glycogenolysis. Thus, in one aspect, disclosed herein are method of reducing/inhibiting/preventing inflammation (such as, for example, acute inflammation, subacute inflammation, chronic inflammation, organ-specific inflammation, systemic inflammation, and/or sepsis) associated hypoglycogenemia in a subject comprising administering to the subject an NTM (such as, for example, SEQ ID NO: 1, SEQ ID NO: 2, SEQ ID NO: 3; SEQ ID NO: 4; SEQ ID NO: 5; SEQ ID NO: 6 or SEQ ID NO: 7, SEQ ID NO: 8, SEQ ID NO: 9, or SEQ ID NO: 16). In one aspect, the methods of reducing/inhibiting/preventing inflammation associated hypoglycogenemia can further comprise the administration of an anti-microbial agent.

"Microbial inflammation" refers to a physical condition associated with its cardinal signs such as redness, swelling, increase in temperature, pain, and impairment of organ function such as impaired respiration as a result of the microvascular endothelial injury in the lungs (and other organs) due to a microbial infection such as a virus, bacteria, fungi, or parasite. The innate and adaptive immune response to infecting pathogen (disease-causing microorganism) can include the burst in production of cytokines, chemokines, and proteolytic enzymes by granulocytes, monocytes, macrophages, dendritic cells, mast cells, innate lymphoid cells, T cells, B cells, NK cells, and NK T cells. Microbial inflammation can be localized to a specific organ- or can be systemic. Microbial inflammation can proceed in stages from acute to subacute and chronic with attendant tissue destruction and subsequent fibrosis. Left unchecked, the acute microbial inflammation can lead to sepsis and septic shock, the end stage of microbial inflammation.

"Microbial inflammation" refers to a mechanism of disease caused by infection ("microbial insult"). It evolves from innate immune response to an infection due to a microbe such as, for example, a virus, bacterium, fungus, or parasite. Thus, the microbial injury caused by microbial virulence factors is aggravated by the host-produced inflammatory mediators that impede the clearance of invading microbes and add insult to organ's injury. It is understood and herein contemplated that the microbial inflammation and its end stage, sepsis can result from any microbial insult elicited by known (or unknown) virulence factors and microbial antigens.

"Pathogen" is an agent that causes infection or disease, especially a virus, bacterium, fungus, protozoa, or parasite.

It is understood that the pathogen can be a virus. Thus in one embodiment the pathogen can be selected from the group consisting of Herpes Simplex virus-1, Herpes Simplex virus-2, Varicella-Zoster virus, Epstein-Barr virus, Cytomegalovirus, Human Herpes virus-6, Variola virus, Vesicular stomatitis virus, Hepatitis A virus, Hepatitis B virus, Hepatitis C virus, Hepatitis D virus, Hepatitis E virus, Rhinovirus, Coronavirus, Influenza virus A, Influenza virus B, Measles virus, Polyomavirus, Human Papillomavirus, Respiratory syncytial virus, Adenovirus, Coxsackie virus, Dengue virus, Mumps virus, Poliovirus, Rabies virus, Rous sarcoma virus, Reovirus, Yellow fever virus, Ebola virus, Marburg virus, Lassa fever virus, Eastern Equine Encephalitis virus, Japanese Encephalitis virus, St. Louis Encephalitis virus, Murray Valley fever virus, West Nile virus, Rift Valley fever virus, Rotavirus A, Rotavirus B, Rotavirus C, Sindbis virus, Simian Immunodeficiency virus, Human T-cell Leukemia virus type-1, Hantavirus, Rubella virus, Simian Immunodeficiency virus, Human Immunodeficiency virus type-1, and Human Immunodeficiency virus type-2.

Also disclosed are methods wherein the pathogen is a bacterium. The pathogen can be selected from the group of bacteria consisting of *Mycobacterium tuberculosis, Mycobacterium bovis, Mycobacterium bovis* strain BCG, BCG substrains, *Mycobacterium avium, Mycobacterium intracellular, Mycobacterium africanum, Mycobacterium kansasii, Mycobacterium marinum, Mycobacterium ulcerans, Mycobacterium avium* subspecies *paratuberculosis, Nocardia asteroides*, other *Nocardia* species, *Legionella pneumophila*, other *Legionella* species, *Actinobacteria baumanii, Salmonella typhi, Salmonella enterica*, other *Salmonella* species, *Shigella boydii, Shigella dysenteriae, Shigella sonnei, Shigella flexneri*, other *Shigella* species, *Yersinia pestis, Pasteurella haemolytica, Pasteurella multocida*, other *Pasteurella* species, *Actinobacillus pleuropneumoniae, Listeria monocytogenes, Listeria ivanovii, Brucella abortus*, other *Brucella* species, *Cowdria ruminantium, Borrelia burgdorferi, Bordetella avium, Bordetella pertussis, Bordetella bronchiseptica, Bordetella trematum, Bordetella hinzii, Bordetella pteri, Bordetella parapertussis, Bordetella ansorpii* other *Bordetella* species, *Burkholderia mallei, Burkholderia psuedomallei, Burkholderia cepacian, Chlamydia pneumoniae, Chlamydia trachomatis, Chlamydia psittaci, Coxiella burnetii, Rickettsial* species, *Ehrlichia* species, *Staphylococcus aureus, Staphylococcus epidermidis, Streptococcus pneumoniae, Streptococcus pyogenes, Streptococcus agalactiae, Escherichia coli, Vibrio cholerae, Campylobacter* species, *Neisseria meningitidis, Neisseria gonorrhea, Pseudomonas aeruginosa*, other *Pseudomonas* species, *Haemophilus influenzae, Haemophilus ducreyi*, other *Hemophilus* species, *Clostridium tetani*, other *Clostridium* species, *Yersinia enterolitica*, and other *Yersinia* species, and *Mycoplasma* species. In one aspect the bacteria is not *Bacillus anthracis*.

Also disclosed are methods wherein the pathogen is a fungus selected from the group of fungi consisting of *Candida albicans, Cryptococcus neoformans, Histoplasma capsulatum, Aspergillus fumigatus, Coccidioides immitis, Paracoccidioides brasiliensis, Blastomyces dermatitis, Pneumocystis carinii, Penicillium marneffi*, and *Alternaria alternata*.

Also disclosed are methods wherein the pathogen is a parasite selected from the group of parasitic organisms consisting of *Toxoplasma gondii, Plasmodium falciparum, Plasmodium vivax, Plasmodium malariae*, other *Plasmodium* species, *Entamoeba histolytica, Naegleria fowleri, Rhodosporidium seeberi, Giardia lamblia, Enterobius ver-*

*micularis, Enterobius gregorii, Ascaris lumbricoides, Ancylostoma duodenale, Necator americanus, Cryptosporidium* spp., *Trypanosoma brucei, Trypanosoma cruzi, Leishmania major*, other *Leishmania* species, *Diphyllobothrium latum, Hymenolepis nana, Hymenolepis diminuta, Echinococcus granulosus, Echinococcus multilocularis, Echinococcus vogeli, Echinococcus oligarthrus, Diphyllobothrium latum, Clonorchis sinensis; Clonorchis viverrini, Fasciola hepatica, Fasciola gigantica, Dicrocoelium dendriticum, Fasciolopsis buski, Metagonimus yokogawai, Opisthorchis viverrini, Opisthorchis felineus, Clonorchis sinensis, Trichomonas vaginalis, Acanthamoeba* species, *Schistosoma intercalatum, Schistosoma haematobium, Schistosoma japonicum, Schistosoma mansoni*, other *Schistosoma* species, *Trichobilharzia regenti, Trichinella spiralis, Trichinella britovi, Trichinella nelsoni, Trichinella nativa*, and *Entamoeba histolytica*.

It is understood and herein contemplated that the microbial inflammation being treated can be in any tissue, organ, or system in the subject where a microbial infection can take place, including, but not limited to the blood, brain, sinuses, upper respiratory tract, or lungs heart, bone marrow, spleen, liver, kidneys, genito-urinary tract, bladder, aural cavities, stomach, intestines, skin, eyes, teeth, or gingiva. Thus, in one aspect, disclosed herein are methods of treating, inhibiting, reducing, or preventing microbial inflammation (such as, for example, acute inflammation, subacute inflammation, chronic inflammation, organ-specific inflammation, systemic inflammation, and/or sepsis) in a subject comprising administering to the subject an anti-microbial agent and a composition comprising one or more NTM, wherein the microbial inflammation is in the blood, brain, sinuses, upper respiratory tract, or lungs, heart, bone marrow, spleen, liver, kidneys, genito-urinary tract, bladder, aural cavities, stomach, intestines, skin, eyes, teeth, or gingiva.

As shown herein, the disclosed NTM (such as, for example, SEQ ID NO: 1, SEQ ID NO: 2, SEQ ID NO: 3; SEQ ID NO: 4; SEQ ID NO: 5; SEQ ID NO: 6 or SEQ ID NO: 7, SEQ ID NO: 8, SEQ ID NO: 9, or SEQ ID NO: 16) can enhance clearance of an infecting microbe even without the presence of an anti-microbial agent and without being directly microbicidal. This clearance can be the result of the ability of the NTM to control the inflammatory response so the host immune system can remove the infecting microbe whereas without the NTM, uncontrolled inflammation (such as, for example, acute inflammation, subacute inflammation, chronic inflammation, organ-specific inflammation, systemic inflammation, and/or sepsis) would proceed, increase, or continue, or by reduction of virulence factors production in the infecting pathogen such a virus, fungus, or protozoa. Accordingly, in one aspect, disclosed herein are methods of reducing the burden of a pathogenic microbe (i.e., clearing the microbe) in the blood, brain, upper respiratory tract including sinuses, and/or lungs, heart, bone marrow, spleen, liver, kidneys, genito-urinary tract, bladder, aural cavities, stomach, intestines, skin, eyes, teeth, and gingiva comprising administering to the subject a therapeutically effective amount of a composition comprising one or more NTM. In one aspect, the methods of reducing/inhibiting the presence of a pathogenic microbe (i.e., clearing the microbe) comprise administering to a subject a composition comprising an NTM but said method does not comprise the administration of an anti-microbial agent. In one aspect, the methods of reducing/inhibiting the presence of a pathogenic microbe (i.e., clearing the microbe) can further comprise the administration of an anti-microbial agent. As used herein, clearance refers to a reduction in the number of infecting microbes at a site of infection such as a tissue, organ, or system (such as for example, blood, upper respiratory tract including sinuses, and/or lungs, brain, bone marrow, spleen, liver, kidneys, genito-urinary tract, bladder, aural cavities, stomach, intestines, skin, eyes, teeth and gingiva). It is understood and herein contemplated that clearance while including the complete or partial elimination of the infecting pathogenic microbe can include less robust reductions in the infecting microbes. Thus, clearance can include such as a 10, 20, 25, 30, 33, 45, 40, 45, 50, 55, 60, 66, 70, 75, 80, 85, 90, 95, 96, 97, 98, or 99% reduction in the numbers of the infecting microbe.

It is understood and herein contemplated that the anti-inflammatory effects observed as a result of the disclosed compositions and used in the disclosed methods treating microbial inflammation can have a therapeutic effect even without the presence of any anti-microbial agent being administered in a composition with and/or in a separate composition from the NTM. Thus, in one aspect, disclosed herein are methods of treating, inhibiting, reducing, and/or preventing microbial inflammation (such as, for example, acute inflammation, subacute inflammation, chronic inflammation, organ-specific inflammation, systemic inflammation, and/or sepsis) in a subject comprising an NTM (such as, for example, SEQ ID NO: 1, SEQ ID NO: 2, SEQ ID NO: 3; SEQ ID NO: 4; SEQ ID NO: 5; SEQ ID NO: 6 or SEQ ID NO: 7, SEQ ID NO: 8, SEQ ID NO: 9, or SEQ ID NO: 16), wherein the methods does not comprise administering an anti-microbial agent either as part of the NTM composition or as a separate administration.

In one aspect, it is understood and herein contemplated that despite being able to reduce inflammation and clear microbes from host tissue, organs, or systems without administration of an anti-microbial agent, the disclosed NTM (such as, for example, SEQ ID NO: 1, SEQ ID NO: 2, SEQ ID NO: 3; SEQ ID NO: 4; SEQ ID NO: 5; SEQ ID NO: 6 or SEQ ID NO: 7, SEQ ID NO: 8, SEQ ID NO: 9, or SEQ ID NO: 16) are not microbicidal. Thus, there can also be situations where the addition of an anti-microbial agent to the treatment regimen such as a component in the composition comprising the NTM or via a separate administration is desired. Accordingly, disclosed herein are methods of treating, inhibiting, reducing, and/or preventing microbial inflammation (such as, for example, acute inflammation, subacute inflammation, chronic inflammation, organ-specific inflammation, systemic inflammation, and/or sepsis) in a subject, comprising administering to the subject an anti-microbial agent and a composition comprising one or more NTM (such as, for example, SEQ ID NO: 1, SEQ ID NO: 2, SEQ ID NO: 3; SEQ ID NO: 4; SEQ ID NO: 5; SEQ ID NO: 6 or SEQ ID NO: 7, SEQ ID NO: 8, SEQ ID NO: 9, or SEQ ID NO: 16). The NTM and anti-microbial agent can be administered as part of the same composition or separately. Examples of anti-microbial agents include but are not limited to antibiotics, antibodies, small molecules, and functional nucleic acids (siRNA, RNAi, anti-sense oligonucleotides), that directly attack the infecting microbe or alter host conditions rendering the host system inhospitable to the microbe.

Furthermore, it is understood and herein contemplated that as the disclosed NTM (such as, for example, SEQ ID NO: 1, SEQ ID NO: 2, SEQ ID NO: 3; SEQ ID NO: 4; SEQ ID NO: 5; SEQ ID NO: 6 or SEQ ID NO: 7, SEQ ID NO: 8, SEQ ID NO: 9, or SEQ ID NO: 16) can, without the aid of an anti-microbial agent, reduce the numbers of infecting microbes and alter the inflammatory milieu such that the host immune system can appropriately fight the infecting microbe, and as these actions are complimentary to the actions of an anti-microbial agent; one way to increase the therapeutic efficacy of an anti-microbial agent is to administer the NTM (such as, for example, SEQ ID NO: 1, SEQ ID NO: 2, SEQ ID NO: 3; SEQ ID NO: 4; SEQ ID NO: 5; SEQ ID NO: 6 or SEQ ID NO: 7, SEQ ID NO: 8, SEQ ID NO: 9, or SEQ ID NO: 16) with the anti-microbial agent. Accordingly, disclosed herein are methods of increasing the therapeutic efficacy of an anti-microbial agent in a subject by further administering to the subject a composition comprising one or more NTM (such as, for example, SEQ ID NO: 1, SEQ ID NO: 2, SEQ ID NO: 3; SEQ ID NO: 4; SEQ ID NO: 5; SEQ ID NO: 6 or SEQ ID NO: 7, SEQ ID NO: 8, SEQ ID NO: 9, or SEQ ID NO: 16). In some aspects of the disclosed treatment methods of increasing the therapeutic efficacy of an anti-microbial agent, an accompanying anti-microbial is a component of the NTM comprising composition. In another aspect, the anti-microbial agent is administered separately from the NTM. Administration of the anti-microbial agent can be prior to, simultaneous with, concurrent with, or following administration of the NTM composition.

As noted above anti-microbial agents can comprise any antibiotics, antibodies, small molecules, and functional nucleic acids (siRNA, RNAi, anti-sense oligonucleotides), that directly attack the infecting microbe or alter host conditions rendering the host system inhospitable to the microbe. Such agents include, but are not limited to Abacavir, Acyclovir, Adefovir, Amantadine, Amprenavir, Ampligen, Arbidol, Atazanavir, Atripla, Balavir, Cidofovir, Combivir, Dolutegravir, Darunavir, Delavirdine, Didanosine, Docosanol, Edoxudine, Efavirenz, Emtricitabine, Enfuvirtide, Entecavir, Ecoliever, Famciclovir, Fomivirsen, Fosamprenavir, Foscarnet, Fosfonet, Ganciclovir, Ibacitabine, Imunovir, Idoxuridine, Imiquimod, Indinavir, Inosine, Lamivudine, Lopinavir, Loviride, Maraviroc, Moroxydine, Methisazone, Nelfinavir, Nevirapine, Nexavir, Nitazoxanide, Norvir, Oseltamivir, Peginterferon alfa-2a, Penciclovir, Peramivir, Pleconaril, Podophyllotoxin, Raltegravir, Ribavirin, Rimantadine, Ritonavir, Pyrimidine, Saquinavir, Sofosbuvir, Stavudine, Telaprevir, Tenofovir, Tenofovir disoproxil, Tipranavir, Trifluridine, Trizivir, Tromantadine, Truvada, Valaciclovir, Valganciclovir, Vicriviroc, Vidarabine, Viramidine, Zalcitabine, Zanamivir, Zidovudine, Clofazimine; Dapsone; Capreomycin; Cycloserine; Ethambutol (Bs); Ethionamide; Isoniazid; Pyrazinamide; Rifampicin; Rifabutin; Rifapentine; Streptomycin; Arsphenamine; Chloramphenicol(Bs); Fosfomycin; Fusidic acid; Metronidazole; Mupirocin; Platensimycin; Quinupristin/Dalfopristin; Thiamphenicol; Tigecycline(Bs); Tinidazole; Trimethoprim(Bs); aminoglycosides such as, for example, Amikacin, Gentamicin, Kanamycin, Meropenem, Neomycin, Netilmicin, Tobramycin, Paromomycin, Streptomycin, Spectinomycin, Nitazoxanide, Melarsoprol Eflornithine, Metronidazole, Tinidazole, Miltefosine, Mebendazole, Pyrantel pamoate, Thiabendazole, Diethylcarbamazine, Ivermectin, Niclosamide, Praziquantel, Albendazole, Praziquantel, Rifampin, Amphotericin B, Fumagillin, Amphotericin B, Candicidin, Filipin, Hamycin, Natamycin, Nystatin, Rimocidin, Bifonazole, Butoconazole, Clotrimazole, Econazole, Fenticonazole, Isoconazole, Ketoconazole, Luliconazole, Miconazole, Omoconazole, Oxiconazole, Sertaconazole, Sulconazole, Tioconazole, Albaconazole, Efinaconazole, Epoxiconazole, Fluconazole, Isavuconazole, Itraconazole, Posaconazole, Propiconazole, Ravuconazole, Terconazole, Voriconazole, Abafungin, Anidulafungin, Caspofungin, Micafungin, Aurones, Benzoic acid, Ciclopirox, Flucytosine, Griseofulvin, Haloprogin, Tolnaftate, Undecylenic acid, Crystal violet, Balsam of Peru, Orotomide, Miltefosine, ansamycins, such as, for example, geldanamycin, rifaximin, herbimycin; Carbapenems, such as, for example, Ertapenem, Doripenem, Imipenem/Cilastatin, and Meropenem; Cephalosporins, such as, for example, Cefadroxil, Cefazolin, Cephradine, Cephapirin, Cephalothin, Cefalexin, Cefaclor, Cefoxitin, Cefotetan, Cefamandole, Cefmetazole, Cefonicid, Loracarbef, Cefprozil, Cefuroxime, Cefixime, Cefdinir, Cefditoren, Cefoperazone, Cefotaxime, Cefpodoxime, Ceftazidime, Ceftibuten, Ceftizoxime, Moxalactam, Ceftriaxone, Cefepime, Ceftaroline fosamil, and Ceftobiprole; Glycopeptides, such as, for example Teicoplanin, Vancomycin, Telavancin, Dalbavancin, and Oritavancin; Lincosamides(Bs), such as, for example, Clindamycin and Lincomycin; Lipopeptides, such as, for example, Daptomycin; Macrolides(Bs), such as, for example, Azithromycin, Clarithromycin, Erythromycin, Roxithromycin, Telithromycin, and Spiramycin; Monobactams, such as, for example, Aztreonam; Nitrofurans, such as, for example, Furazolidone and Nitrofurantoin(Bs); Oxazolidinones(Bs), such as, for example, Linezolid, Posizolid, Radezolid, and Torezolid; Penicillins, such as, for example, Amoxicillin, Ampicillin, Azlocillin, Dicloxacillin, Flucloxacilline, Mezlocillin, Methicillin, Nafcillin, Oxacillin, Penicillin G, Penicillin V, Piperacillin, Penicillin G, Temocillin, and Ticarcillin; Polypeptides, such as, for example, Bacitracin, Colistin, and Polymyxin B; Quinolones/Fluoroquinolones, such as, for example, Ciprofloxacin, Enoxacin, Gatifloxacin, Gemifloxacin, Levofloxacin, Lomefloxacin, Moxifloxacin, Nadifloxacin, Nalidixic acid, Norfloxacin, Ofloxacin, Trovafloxacin, Grepafloxacin, Sparfloxacin, and Temafloxacin; Sulfonamides(Bs), such as, for example, Mafenide, Sulfacetamide, Sulfadiazine, Silver sulfadiazine, Sulfadimethoxine, Sulfamethizole, Sulfamethoxazole, Sulfanilamide (archaic), Sulfasalazine, Sulfisoxazole, Trimethoprim-Sulfamethoxazole (Co-trimoxazole) (TMP-SMX), and Sulfonamidochrysoidine (archaic); Tetracyclines (Bs), such as, for example, Demeclocycline, Doxycycline, Metacycline, Minocycline, Oxytetracycline, and Tetracycline; monoclonal antibodies such as, for example, Actoxumab, Atidortoxumab, Berlimatoxumab, Bezlotoxumab, Cosfroviximab, Edobacomab, Felvizumab, Firivumab, Foravirumab, Larcaviximab, Motavizumab, Navivumab, Panobacumab, Palivizumab, Porgaviximab, CR6261, Rafivirumab, Pagibaximab, Obiltoxaximab, Ibalizumab, Regavirumab, Rmab, Sevirumab, Rivabazumab pegol, Tefibazumab, Suvratoxumab, and Tuvirumab; and checkpoint inhibitors; Pembrolizumab, Nivolumab, Atezolizumab, Avelumab, Durvalumab, pidilizumab, AMP-224, AMP-514, PDR001, cemiplimab, and Ipilimumab.

In one aspect, it is understood and herein contemplated that the disclosed methods of treating microbial inflammation (such as, for example, acute inflammation, subacute inflammation, chronic inflammation, organ-specific inflammation, systemic inflammation, and/or sepsis) are, in addition to the effects of the anti-microbial, the results of the NTM controlling the nuclear transport shuttles and thus preventing the unchecked inflammatory response. Accordingly, disclosed herein are methods of reducing levels of a Stress Responsive Transcription Factor (SRTF) (such as, for example, NF-κB (including NF-κB is NF-κB 1, NF-κB A or a combination thereof), STAT1α, and/or AP-1) and/or metabolic transcription factors such as Sterol-Regulatory Element Binding Proteins (SREBPs) 1a, 1c, and 2 in a cell at a site of inflammation in a subject with an infection, comprising administering to the subject a therapeutically effective amount of a composition comprising one or more Nuclear Transport Modifiers (NTMs) such as, for example, SEQ ID NO: 1, SEQ ID NO: 2, SEQ ID NO: 3; SEQ ID NO: 4; SEQ ID NO: 5; SEQ ID NO: 6 or SEQ ID NO: 7, SEQ ID NO: 8, SEQ ID NO: 9, or SEQ ID NO: 16. In one aspect, the cell where the SRTF is being reduced is a macrophage, B cell, NK cell, NK T cell, T cell, endothelial cell, or epithelial cell.

Pharmaceutical Carriers/Delivery of Pharmaceutical Products

Compositions, e.g., pharmaceutical compositions, described herein for treating microbial inflammation in a subject (e.g., a human subject) include a therapeutically effective amount of a Nuclear Transport Modifier (such as cSN50, cSN50.1, cSN50.1 beta, or a NTM as set forth in SEQ ID NO: 3, SEQ ID NO: 4, SEQ ID NO: 5, SEQ ID NO: 6, SEQ ID NO: 7, SEQ ID NO: 8, and/or SEQ ID NO: 9) sufficient for treating microbial inflammation (including treating thrombocytopenia or hypoglycogenemia resulting from said microbial inflammation) and/or reducing the burden of a pathogenic microbe in a tissue, organ, or system and a pharmaceutically acceptable carrier. Similarly, compositions described herein for treating microbial inflammation in a subject (e.g., a human subject) include a therapeutically effective amount of a Nuclear Transport Modifier (such as cSN50, cSN50.1, cSN50.1 beta, or a NTM as set forth in SEQ ID NO: 3, SEQ ID NO: 4, SEQ ID NO: 5, SEQ ID NO: 6, SEQ ID NO: 7, SEQ ID NO: 8, and/or SEQ ID NO: 9) sufficient for reducing nuclear levels of a SRTF and SREBPs in a subject with microbial inflammation and a pharmaceutically acceptable carrier. In some aspect, the composition does not further comprise an anti-microbial agent.

It is understood and herein contemplated that despite the ability of the disclosed compositions to inhibit microbial virulence and effectuate microbial clearance in tissue without the addition of an anti-microbial agent, there can be instances where the addition (either in the composition itself or as a separate administration) of an anti-microbial is desired. Accordingly, disclosed herein are methods of treating, inhibiting, reducing, or preventing microbial inflammation in a subject, wherein the method comprises administering to the subject an anti-microbial agent.

As described above, the compositions can also be administered in vivo in a pharmaceutically acceptable carrier. By "pharmaceutically acceptable" is meant a material that is not biologically or otherwise undesirable, i.e., the material may be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The compositions may be administered orally, parenterally (e.g., intravenously), by intramuscular injection, by intraperitoneal injection, transdermally, extracorporeally, topically or the like, including topical intranasal administration or administration by inhalant. As used herein, "topical intranasal administration" means delivery of the compositions into the nose and nasal passages through one or both of the nares and can comprise delivery by a spraying mechanism or droplet mechanism, or through aerosolization of the nucleic acid or vector. Administration of the compositions by inhalant can be through the nose or mouth via delivery by a spraying or droplet mechanism. Delivery can also be directly to any area of the respiratory system (e.g., lungs) via intubation. The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein.

Compositions for parenteral use may be provided in unit dosage forms (e.g., in single-dose ampoules), or in vials containing several doses and in which a suitable preservative may be added (see below). The composition may be in the form of a solution, a suspension, an emulsion, an infusion device, or a delivery device for implantation, or it may be presented as a dry powder to be reconstituted with water or another suitable vehicle before use. Apart from the active agent that treats microbial inflammation the composition may include suitable parenterally acceptable carriers and/or excipients. The active therapeutic agent(s) may be incorporated into microspheres, microcapsules, nanoparticles, liposomes, or the like for controlled release. Furthermore, the composition may include suspending, solubilizing, stabilizing, pH-adjusting agents, tonicity adjusting agents, and/or dispersing agents.

The materials may be in solution, suspension (for example, incorporated into microparticles, liposomes, or cells). These may be targeted to a particular cell type via antibodies, receptors, or receptor ligands. The following references are examples of the use of this technology to target specific proteins to tumor tissue (Senter, et al., *Bioconjugate Chem.*, 2:447-451, (1991); Bagshawe, K. D., *Br. J. Cancer*, 60:275-281, (1989); Bagshawe, et al., *Br. J. Cancer*, 58:700-703, (1988); Senter, et al., *Bioconjugate Chem.*, 4:3-9, (1993); Battelli, et al., *Cancer Immunol. Immunother.*, 35:421-425, (1992); Pietersz and McKenzie, *Immunolog. Reviews*, 129:57-80, (1992); and Roffler, et al., Biochem. Pharmacol, 42:2062-2065, (1991)). Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., *Cancer Research*, 49:6214-6220, (1989); and Litzinger and Huang, *Biochimica et Biophysica Acta*, 1104:179-187, (1992)).

a) Pharmaceutically Acceptable Carriers

The compositions, including antibodies, can be used therapeutically in combination with a pharmaceutically acceptable carrier.

Suitable carriers and their formulations are described in *Remington: The Science and Practice of Pharmacy* (19th ed.) ed. A. R. Gennaro, Mack Publishing Company, Easton, PA 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, antiinflammatory agents, anesthetics, and the like.

The pharmaceutical composition may be administered in a number of ways depending on whether local or systemic treatment is desired, and on the area to be treated. Administration may be topically (including ophthalmically, vaginally, rectally, intranasally), orally, by inhalation, or parenterally, for example by intravenous drip, subcutaneous, intraperitoneal or intramuscular injection using a two-compartment injector. The disclosed antibodies can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Materials for use in the preparation of microspheres and/or microcapsules are, e.g., biodegradable/bioerodible polymers such as polyglactin, poly-(isobutyl cyanoacrylate), poly(2-hydroxyethyl-L-glutamine), and poly(lactic acid). Biocompatible carriers that may be used when formulating a controlled release parenteral formulation are carbohydrates (e.g., dextrans), proteins (e.g., albumin), lipoproteins, or antibodies. Materials for use in implants can be non-biodegradable (e.g., polydimethyl siloxane) or biodegradable (e.g., poly(caprolactone), poly(lactic acid), poly(glycolic acid) or poly(ortho esters) or combinations thereof).

Formulations for oral use include tablets containing the active ingredient(s) (e.g., cSN50, cSN50.1, cSN50.1 beta, or a NTM as set forth in SEQ ID NO: 3, SEQ ID NO: 4, SEQ ID NO: 5, SEQ ID NO: 6, SEQ ID NO: 7, SEQ ID NO: 8, and/or SEQ ID NO: 9) in a mixture with non-toxic pharmaceutically acceptable excipients. Such formulations are known to the skilled artisan. Excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

The tablets may be uncoated or they may be coated by known techniques, optionally to delay disintegration and absorption in the gastrointestinal tract and thereby providing a sustained action over a longer period. The coating may be adapted to release the active drug in a predetermined pattern (e.g., in order to achieve a controlled release formulation) or it may be adapted not to release the active drug until after passage of the stomach (enteric coating). The coating may be a sugar coating, a film coating (e.g., based on hydroxypropyl methylcellulose, methylcellulose, methyl hydroxyethyl cellulose, hydroxypropylcellulose, carboxymethylcellulose, acrylate copolymers, polyethylene glycols and/or polyvinylpyrrolidone), or an enteric coating (e.g., based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose). Furthermore, a time delay material, such as, e.g., glyceryl monostearate or glyceryl distearate may be employed.

The solid tablet compositions may include a coating adapted to protect the composition from unwanted chemical changes, (e.g., chemical degradation prior to the release of the active therapeutic substance). The coating may be applied on the solid dosage form in a similar manner as that described in Swarbrick, J. and Boylan, J. C., supra. At least two therapeutics (e.g., a composition including cSN50, cSN50.1 or any of the NTM as set forth in SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 16, as well as any anti-microbial) may be mixed together in the tablet, or may be partitioned. In one example, the first active therapeutic is contained on the inside of the tablet, and the second active therapeutic is on the outside, such that a substantial portion of the second active therapeutic is released prior to the release of the first active therapeutic.

Formulations for oral use may also be presented as chewable tablets, or as hard gelatin capsules wherein the active ingredient is mixed with an inert solid diluent (e.g., potato starch, lactose, microcrystalline cellulose, calcium carbonate, calcium phosphate or kaolin), or as soft gelatin capsules wherein the active ingredient is mixed with water or an oil medium, for example, peanut oil, liquid paraffin, or olive oil. Powders and granulates may be prepared using the ingredients mentioned above under tablets and capsules in a conventional manner using, e.g., a mixer, a fluid bed apparatus or a spray drying equipment. Compositions as described herein can also be formulated for inhalation and topical applications. Optionally, an anti-microbial agent may be administered in combination with the NTM; such methods are known to the skilled artisan (see, e.g., Gennaro, supra). Combinations are expected to be advantageously synergistic.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

b) Therapeutic Uses

Effective dosages and schedules for administering the compositions may be determined empirically, and making such determinations is within the skill in the art. The dosage ranges for the administration of the compositions are those large enough to produce the desired effect in which the symptoms of the disorder are effected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counter indications. Dosage can vary, and can be administered in one or more dose administrations daily, for one or several days. Guidance can be found in the literature for appropriate dosages for given classes of pharmaceutical products. For example, guidance in selecting appropriate doses for antibodies can be found in the literature on therapeutic uses of antibodies, e.g., *Handbook of Monoclonal Antibodies*, Ferrone et al., eds., Noges Publications, Park Ridge, N.J., (1985) ch. 22 and pp. 303-357; Smith et al., *Antibodies in Human Diagnosis and Therapy*, Haber et al., eds., Raven Press, New York (1977) pp. 365-389. A typical daily dosage of the antibody used alone might range from about 1 µg/kg to up to 100 mg/kg of body weight or more per day, depending on the factors mentioned above.

2. Homology/Identity

It is understood that one way to define any known variants and derivatives or those that might arise, of the disclosed genes and proteins herein is through defining the variants and derivatives in terms of homology to specific known sequences. For example SEQ ID NO: 2 sets forth a particular sequence of an NTM (cSN50.1). Specifically disclosed are variants of these and other genes and proteins herein disclosed which have at least, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 percent homology to the stated sequence. Those of skill in the art readily understand how to determine the homology of two proteins or nucleic acids, such as genes. For example, the homology can be calculated after aligning the two sequences so that the homology is at its highest level. As used herein, sequence homology is used interchangeably with sequence identity.

Another way of calculating homology can be performed by published algorithms. Optimal alignment of sequences for comparison may be conducted by the local homology algorithm of Smith and Waterman *Adv. Appl. Math.* 2: 482 (1981), by the homology alignment algorithm of Needleman and Wunsch, *J. MoL Biol.* 48: 443 (1970), by the search for similarity method of Pearson and Lipman, *Proc. Natl. Acad. Sci. U.S.A.* 85: 2444 (1988), by computerized implementations of these algorithms (GAP, BESTFIT, FASTA, and TFASTA in the Wisconsin Genetics Software Package, Genetics Computer Group, 575 Science Dr., Madison, WI), or by inspection.

The same types of homology can be obtained for nucleic acids by for example the algorithms disclosed in Zuker, M. *Science* 244:48-52, 1989, Jaeger et al. *Proc. Natl. Acad. Sci. USA* 86:7706-7710, 1989, Jaeger et al. *Methods Enzymol.* 183:281-306, 1989 which are herein incorporated by reference for at least material related to nucleic acid alignment.

3. Peptides a) Protein Variants

As discussed herein there are numerous variants of the NTM that are known and herein contemplated. Protein variants and derivatives are well understood to those of skill in the art and in can involve amino acid sequence modifications. For example, amino acid sequence modifications typically fall into one or more of three classes: substitutional, insertional or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Cell-penetrating fusion protein derivatives, are made by fusing a polypeptide sufficiently large to confer intracellular delivery of the targeting sequence by cross-linking in vitro or by recombinant cell culture transformed with DNA encoding the fusion. Deletions are characterized by the removal of one or more amino acid residues from the protein sequence. Typically, no more than about from 2 to 6 residues are deleted at any one site within the protein molecule. These variants ordinarily are prepared by site specific mutagenesis of nucleotides in the DNA encoding the protein, thereby producing DNA encoding the variant, and thereafter expressing the DNA in recombinant cell culture. Techniques for making substitution mutations at predetermined sites in DNA having a known sequence are well known, for example M13 primer mutagenesis and PCR mutagenesis. Amino acid substitutions are typically of single residues, but can occur at a number of different locations at once; insertions usually will be on the order of about from 1 to 10 amino acid residues; and deletions will range about from 1 to 30 residues. Deletions or insertions preferably are made in adjacent pairs, i.e. a deletion of 2 residues or insertion of 2 residues. Substitutions, deletions, insertions or any combination thereof may be combined to arrive at a final construct. The mutations must not place the sequence out of reading frame and preferably will not create complementary regions that could produce secondary mRNA structure. Substitutional variants are those in which at least one residue has been removed and a different residue inserted in its place. Such substitutions generally are made in accordance with the following Tables 2 and 3 and are referred to as conservative substitutions.

TABLE 2

Amino Acid Abbreviations

| Amino Acid | Abbreviations | |
|---|---|---|
| Alanine | Ala | A |
| allosoleucine | AIle | |
| Arginine | Arg | R |
| asparagine | Asn | N |
| aspartic acid | Asp | D |
| Cysteine | Cys | C |
| glutamic acid | Glu | E |
| Glutamine | Gln | Q |
| Glycine | Gly | G |
| Histidine | His | H |
| Isolelucine | Ile | I |
| Leucine | Leu | L |
| Lysine | Lys | K |
| phenylalanine | Phe | F |
| proline | Pro | P |
| pyroglutamic acid | pGlu | |
| Serine | Ser | S |
| Threonine | Thr | T |
| Tyrosine | Tyr | Y |
| Tryptophan | Trp | W |
| Valine | Val | V |

TABLE 3

Amino Acid Substitutions Original Residue Exemplary Conservative Substitutions, others are known in the art.

| | |
|---|---|
| Ala | Ser |
| Arg | Lys; Gln |
| Asn | Gln; His |
| Asp | Glu |
| Cys | Ser |
| Gln | Asn, Lys |
| Glu | Asp |
| Gly | Pro |
| His | Asn; Gln |
| Ile | Leu; Val |
| Leu | Ile; Val |
| Lys | Arg; Gln |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Substantial changes in function or immunological identity are made by selecting substitutions that are less conservative than those in Table 3, i.e., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions which in general are expected to produce the greatest changes in the protein properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine, in this case, (e) by increasing the number of sites for sulfation and/or glycosylation.

For example, the replacement of one amino acid residue with another that is biologically and/or chemically similar is known to those skilled in the art as a conservative substitution. For example, a conservative substitution would be replacing one hydrophobic residue for another, or one polar residue for another. The substitutions include combinations such as, for example, Gly, Ala; Val, Ile, Leu; Asp, Glu; Asn, Gln; Ser, Thr; Lys, Arg; and Phe, Tyr. Such conservatively substituted variations of each explicitly disclosed sequence are included within the mosaic polypeptides provided herein.

Substitutional or deletional mutagenesis can be employed to insert sites for N-glycosylation (Asn-X-Thr/Ser) or O-glycosylation (Ser or Thr). Deletions of cysteine or other labile residues also may be desirable. Deletions or substitutions of potential proteolysis sites, e.g. Arg, is accomplished for example by deleting one of the basic residues or substituting one by glutaminyl or histidyl residues.

Certain post-translational derivatizations are the result of the action of recombinant host cells on the expressed polypeptide. Glutaminyl and asparaginyl residues are frequently post-translationally deamidated to the corresponding glutamyl and aspartyl residues. Alternatively, these residues are deamidated under mildly acidic conditions. Other post-translational modifications include hydroxylation of proline and lysine, phosphorylation of hydroxyl groups of seryl or threonyl residues, methylation of the o-amino groups of lysine, arginine, and histidine side chains (T. E. Creighton, Proteins: Structure and Molecular Properties, W. H. Freeman & Co., San Francisco pp 79-86 [1983]), acetylation of the N-terminal amine and, in some instances, amidation of the C-terminal carboxyl.

It is understood that one way to define the variants and derivatives of the disclosed protein-derived peptides herein is through defining the variants and derivatives in terms of homology/identity to specific known sequences. For example, SEQ ID NO:2 sets forth a particular sequence of cSN50.1. Specifically disclosed are variants of these and other proteins herein disclosed which have at least, 70%, 75%, 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, or 100% sequence identity to the stated sequence. Those of skill in the art readily understand how to determine the homology of two proteins. For example, the homology can be calculated after aligning the two sequences so that the homology is at its highest level.

Another way of calculating homology can be performed by published algorithms. Optimal alignment of sequences for comparison may be conducted by the local homology algorithm of Smith and Waterman Adv. Appl. Math. 2: 482 (1981), by the homology alignment algorithm of Needleman and Wunsch, J. MoL Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, WI), or by inspection.

The same types of homology can be obtained for nucleic acids by for example the algorithms disclosed in Zuker, M. Science 244:48-52, 1989, Jaeger et al. Proc. Natl. Acad. Sci. USA 86:7706-7710, 1989, Jaeger et al. Methods Enzymol. 183:281-306, 1989.

It is understood that the description of conservative mutations and homology can be combined together in any combination, such as embodiments that have at least 70% homology to a particular sequence wherein the variants are conservative mutations.

As this specification discusses various proteins and protein sequences it is understood that the nucleic acids that can encode those protein sequences are also disclosed. This would include all degenerate sequences related to a specific protein sequence, i.e. all nucleic acids having a sequence that encodes one particular protein sequence as well as all nucleic acids, including degenerate nucleic acids, encoding the disclosed variants and derivatives of the protein sequences. Thus, while each particular nucleic acid sequence may not be written out herein, it is understood that each and every sequence is in fact disclosed and described herein through the disclosed protein sequence.

It is understood that there are numerous amino acid and peptide analogs which can be incorporated into the disclosed compositions. For example, there are numerous D amino acids or amino acids which have a different functional substituent then the amino acids shown in Table 2 and Table 3. The opposite stereo isomers of naturally occurring peptides are disclosed, as well as the stereo isomers of peptide analogs. These amino acids can readily be incorporated into polypeptide chains by charging tRNA molecules with the amino acid of choice and engineering genetic constructs that utilize, for example, amber codons, to insert the analog amino acid into a peptide chain in a site specific way.

Molecules can be produced that resemble peptides, but which are not connected via a natural peptide linkage. For example, linkages for amino acids or amino acid analogs can include $CH_2NH$—, —$CH_2S$—, —$CH_2$—$CH_2$—$CH$=$CH$— (cis and trans), —$COCH_2$—, —$CH(OH)CH_2$—, and —$CHH_2SO$— (These and others can be found in Spatola, A. F. in *Chemistry and Biochemistry of Amino Acids, Peptides, and Proteins*, B. Weinstein, eds., Marcel Dekker, New York, p. 267 (1983); Spatola, A. F., *Vega Data* (March 1983), Vol. 1, Issue 3, Peptide Backbone Modifications (general review); Morley, *Trends Pharm Sci* (1980) pp. 463-468; Hudson, D. et al., Int J Pept Prot Res 14:177-185 (1979) (—$CH_2NH$—, $CH_2CH_2$—); Spatola et al. *Life Sci* 38:1243-1249 (1986) (—$CHH_2$—S); Hann *J. Chem. Soc Perkin Trans*. I 307-314 (1982) (—CH—CH—, cis and trans); Almquist et al. *J. Med. Chem.* 23:1392-1398 (1980) (—$COCH_2$—); Jennings-White et al. *Tetrahedron Lett* 23:2533 (1982) (—$COCH_2$—); Szelke et al. European Appln, EP 45665 CA (1982): 97:39405 (1982) (—CH(OH) $CH_2$—); Holladay et al. *Tetrahedron*. Lett 24:4401-4404 (1983) (—C(OH)$CH_2$—); and Hruby *Life Sci* 31:189-199 (1982) (—$CH_2$—S—); each of which is incorporated herein by reference. A particularly preferred non-peptide linkage is —$CH_2NH$—. It is understood that peptide analogs can have more than one atom between the bond atoms, such as b-alanine, g-aminobutyric acid, and the like.

Amino acid analogs and analogs and peptide analogs often have enhanced or desirable properties, such as, more economical production, greater chemical stability, enhanced pharmacological properties (half-life, absorption, potency, efficacy, etc.), altered specificity (e.g., a broad-spectrum of biological activities), reduced antigenicity, and others.

D-amino acids can be used to generate more stable peptides, because D amino acids are not recognized by peptidases and such. Systematic substitution of one or more amino acids of a consensus sequence with a D-amino acid of the same type (e.g., D-lysine in place of L-lysine) can be used to generate more stable peptides. Cysteine residues can be used to cyclize or attach two or more peptides together. This can be beneficial to constrain peptides into particular conformations. Stapled alpha-helical sequence of signal-sequence hydrophobic region can be used to stabilize its membrane-translocating conformation in NTM.

C. Examples

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. Example 1: Survival, Clearance, and Thrombocytopenia are Improved in Polymicrobial Sepsis by Targeting Nuclear Transport Shuttles Herein is reported that in an experimental model of polymicrobial sepsis, simultaneous targeting of nuclear transport adaptors Imp α5 and Imp β1 with cSN50.1 attenuated nuclear import of SRTFs and maintained metabolically-important glycogen stores in the liver. NTM treatment led to a significantly reduced bacterial burden in blood, spleen, and lungs, attenuated proinflammatory cytokines and chemokines in blood, preserved normal platelet count in blood, and reduced plasma markers of microvascular injury as well as neutrophil infiltration of the liver. Moreover, combining NTM with antibiotic therapy significantly extended mean time to death, and almost doubled survival.

a) Results (1) NTM Attenuates Nuclear Transport of SRTFs in Liver Cells and Reduces Bacterial Burden in Blood, Spleen, and Lungs of Septic Mice As Gram-negative bacteria are the causes of sepsis in two-thirds of patients either alone or in combination with other microbes, a clinically relevant model of polymicrobial sepsis was employed. In this non-surgical model, polymicrobial peritonitis is induced by standardized challenge with bacteria-rich gut microbiome. Freshly obtained gut microbiome, in the form of a cecal slurry (CS), was injected intraperitoneally thereby avoiding surgical wounding and uncontrolled spillage of cecal contents into the peritoneal cavity inherent to surgical cecal ligation and puncture. The hypothesis that controlling nuclear import of SRTFs with cSN50.1, the newest, highly soluble cell-penetrating NTM peptide, can reduce production of sepsis-associated mediators of microvascular injury, improve the clearance of bacteria in blood and major organs, and increase the effectiveness of antimicrobial therapy thereby improving survival was tested.

Patients who succumb to sepsis display strikingly increased levels of a key SRTF, NF-κB, in nuclei of peripheral blood mononuclear cells. Consistent with this clinical hallmark, not only was increased nuclear content of NF-κB1 (p50) and NF-κB RelA (p65) found, but also phosphorylated STAT1α (MW91), phosphorylated STAT1β (MW84) and AP-1 (cFos) in liver cells of septic animals comprising hepatocytes, macrophages, and microvascular endothelial cells, among other cells (FIG. 2A). Treatment with NTM significantly reduced the nuclear content of NF-κB1 (p50) and NF-κB RelA (p65), phosphorylated STAT1α and AP-1 (cFos) (FIG. 2B). STAT1β was not reduced by NTM treatment. Though tyrosine phosphorylation of both STAT1α and β is induced by the inflammatory cytokine IFN-γ, STAT1β is a transcriptionally inactive truncated isoform and acts as a dominant-negative inhibitor of STAT1α. Proinflammatory signaling to the nucleus has also been implicated in rapid glycogen depletion in the liver during sepsis. Accordingly, NTM treatment prevented glycogenolysis in the livers of infected mice, demonstrated by Periodic Acid-Schiff stain (PAS) (FIG. 2C). In earlier studies of lipopolysaccharide toxemia, NTM also prevented glycogen depletion from liver.

Efficient microbial clearance is essential for survival from polymicrobial sepsis. Remarkably, in the absence of antimicrobial therapy, CS-infected mice treated with NTM-displayed enhanced bacterial clearance from blood and target organs (spleen and lung) by 12 h after infection (FIG. 3). A direct antimicrobial effect of NTM can be excluded as cSN50.1 peptide did not inhibit the growth of cecal bacteria tested ex vivo. The most dramatic reduction in bacterial load (about 700-fold) was noted in the lungs while bacteria in spleen and blood were also significantly reduced. Negligible detection of bacteria in sham-infected animals can be attributed to multiple intraperitoneal injections and repeated blood collections. These results indicate that the function of blood-borne and tissue phagocytes in regard to bacterial clearance is preserved, or even enhanced, when proinflammatory signaling to the nucleus is reduced in NTM-treated infected animals.

(2) NTM Attenuates Inflammatory Mediators and their Downstream Effects on Immune Signaling During the early hyperinflammatory phase of sepsis, plasma levels of proinflammatory cytokines TNF-α and IL-6, as well as the chemokine monocyte chemoattractant protein 1 (MCP-1/CCL2), are dramatically increased. In concert, the type II interferon, interferon gamma (IFN-γ), enhances cell-mediated immune responses. IFN-γ is a specific activator of macrophage function and plays a regulatory role in the host immune defense to bacterial infection. Remarkably, administration of anti-IFN-γ antibody significantly decreased bacterial load in the peritoneum in a rat model of peritonitis. Reduced expression of vascular endothelial (VE) cadherin, the mainstay of microvascular integrity, was observed in IFN-γ-stimulated human pulmonary microvascular endothelial cells and in the endothelium of all vessels obtained from patients with Gram-negative bacterial sepsis complicated by Acute Respiratory Distress Syndrome (ARDS). Production of anti-inflammatory cytokines, such as IL-10, is also triggered to restore inflammatory homeostasis. While increased IL-10 provides a feedback mechanism to suppress TNF-α expression and counteract excessive immune responses, overproduction of IL-10 reduces bacterial clearance. Continued overexpression of IL-10 contributes to the immunosuppressive environment that characterizes later stages of sepsis. However, if excessive production of inflammatory mediators prevails, the consequences are vascular dysfunction, multi-organ failure and death. The attenuation of nuclear signaling mediated by SRTFs was accompanied by significant suppression of plasma levels of TNF-α, MCP-1, and IFN-γ, whereas the pattern of IL-6 response remained unchanged (FIG. 4A). Cumulatively, the sepsis-induced proinflammatory response, with the notable exception of IL-6, is suppressed by NTM, contributing to maintaining homeostatic regulation.

Consistent with the role of phagocytes in bacterial clearance from blood and organs, both vehicle and cSN50.1-treated animals displayed a significant increase in total circulating leukocytes compared to sham-infected animals at 12 hours after sepsis was initiated, indicating that lymphocyte, neutrophil and monocyte counts were not suppressed by treatment with NTM (cSN50.1) (FIG. 4B). Strikingly, NTM preserved platelet counts (FIG. 4B) while thrombocytopenia, manifested by a drop in platelet count in blood, was evident in vehicle-treated mice. This hallmark of severe bacterial infection is a marker of poor outcome, presumably due to platelet entrapment by injured microvascular surfaces and subsequent formation of platelet thrombi. Acute platelet consumption and microvascular dysfunction depend on induction of genomic reprogramming regulated by SRTFs and controlled by their nuclear import. Other parameters of the complete blood count were not significantly altered by infection or NTM treatment (FIG. 5).

Selectins play a critical role in inflammation by regulating tethering and rolling of neutrophils along the microvascular endothelium, a prerequisite for subsequent adhesion and emigration. Leukocyte migration appears to be the initial event that leads to multiple organ inflammation and dysfunction during sepsis. Interfering with selectin-mediated rolling of leukocytes prevents their extravascular migration and subsequent organ dysfunction. L-selectin is constitutively expressed on leukocytes and is rapidly released to the bloodstream in response to activation. E-selectin is not stored in endothelial cells; rather it is expressed due to genomic upregulation evoked by lipopolysaccharide, the primary virulence factor of Gram-negative bacteria, and by cytokines, such as TNF-α. E-selectin is then released into the bloodstream. P-selectin is expressed by activated platelets and endothelial cells, mediating platelet-leukocyte and platelet-endothelial cell interactions and contributing to thrombi formation. NTM, in addition to antibiotic treatment, attenuated expression of soluble P-selectin in blood plasma and prevented elevation of soluble E-selectin, while plasma levels of these markers of endothelial damage continued to rise with antibiotic treatment alone (FIG. 4C).

Consistent with reduced cytokine, chemokine and selectins production, NTM treatment inhibited liver infiltration by neutrophils (FIG. 4D). Migration of neutrophils into the hepatic parenchyma was not observed in the sham-infected animals. In infected mice treated with vehicle, increased numbers of neutrophils were observed in the hepatic parenchyma, indicating systemic inflammation. In contrast, CS-infected mice treated with NTM displayed neutrophils aggregated mostly on the serosal surface with a few cells in the hepatic parenchyma, indicating localized inflammation in the peritoneal cavity following the intraperitoneal injection of gut microbiome in the form of standardized "Cecal Slurry" (CS).

Cumulatively, these parameters of microvascular inflammation were significantly suppressed when infected mice were treated with NTM either alone or in combination with antimicrobial therapy, further indicating the overall dependence of this process on the nuclear transport of SRTFs.

(3) Nuclear Signaling Modulation in Combination with Antimicrobial Therapy Increases Survival in Sepsis Next was asked whether the beneficial actions of NTM in the acute phase of polymicrobial sepsis can exert a positive effect on overall survival in sepsis. To test this hypothesis, NTM treatment was combined with antimicrobial therapy in a model of polymicrobial sepsis. As documented in FIG. 6, survival among animals treated only with meropenem, a broad-spectrum β-lactam antibiotic commonly used to treat severe infections, was 30% with median survival at 42 h. In contrast, when meropenem treatment was combined with NTM, survival was significantly increased to 55% and mean time to death was extended to 83 h (FIG. 6). This gain in survival indicates that targeting proinflammatory nuclear signaling with NTM prevents irreversible multiple organ injury in sepsis when runaway infection cannot be controlled by antimicrobial therapy alone.

b) Discussion

This study demonstrates that the dynamics and outcome of polymicrobial sepsis in a clinically relevant experimental model can be improved by targeting nuclear transport of stress-responsive transcription factors responsible for the genomic storm triggered by microbial virulence factors and endogenous mediators. Sepsis-induced signaling to the nucleus is responsible for blood and vascular system responses that contribute to multiple organ failure. Mechanistically, NTM penetrates the plasma membrane of several cell types involved in sepsis and targets Imp α5 and Imp β1 responsible for nuclear signaling mediated by the translocation of SRTFs and SREBPs from the cytoplasm to the nucleus, respectively. The nuclear transport of SRTFs and SREBPs is an attractive target for therapeutic intervention, as selective targeting of Imp α5 and Imp β1 by the NTM, cSN50.1 peptide, suppresses activation of a myriad of proinflammatory and metabolic genes regulated by both groups of transcription factors. By impeding nuclear import of NFκB and other SRTFs (AP-1 and STAT1), NTM suppressed expression of proinflammatory mediators including cytokines, chemokines, and soluble forms of cell adhesion molecules (selectins). Notably, NTM treatment in the absence of antimicrobial therapy enhanced clearance of multiple microbial species derived from the gut microbiome. This was especially notable in lungs wherein a 700-fold reduction in bacterial burden was obtained. Such an effect of NTM treatment can be linked to early suppression of IL-10, which has been demonstrated to impair the phagocytic function of alveolar macrophages. Thus, NTM-enhanced bacterial clearance indicates that this mode of targeting nuclear transport is not detrimental to the function of phagocytic cells in lungs and other organs, or to blood bactericidal activity. Of note, cell type-specific gene ablation of Toll-like receptor-4 (TLR4) in hepatocytes led to enhanced macrophage phagocytosis, lower bacterial levels, and improved survival in a model of polymicrobial sepsis caused by cecal ligation and puncture without antibiotic therapy. Thus, NTM targeting of nuclear transport achieves a similar outcome as genetic ablation of TLR4 in terms of bacterial clearance.

TLR4 is a canonical receptor for LPS, a virulence factor known as the most active biologic inducer of systemic inflammation. LPS expressed by Gram-negative bacteria is highly diverse, displaying striking structural diversity and corresponding biologic activity, as exemplified by *Escherichia coli* and *Neisseria meningitides*. Analysis of systemic inflammation induced by LPS derived from a single bacterial species provides valuable information about the mechanism of action of that particular LPS. However, a polymicrobial sepsis model such as the one used in this study, which is based on intraperitoneal injection of gut microbiome ("cecal slurry"), infects the host with a multitude of Gram-negative bacteria expressing diverse LPS structures and additional virulence factors as well as Gram-positive bacteria and other microbes. Therefore, this clinically-relevant model raises the stakes for the host's defenses and poses a greater challenge for testing new and more effective countermeasures.

In this complex setting of polymicrobial sepsis, targeting of the nuclear transport checkpoint (see FIG. 1) offers a conceptual advantage. This checkpoint controls the traffic of stress-responsive transcription factors that display NLSs, recognized and ferried by nuclear transport shuttles from the cytoplasm to the nucleus. A family of six importins α are the mainstays of nuclear transport in mammalian cells. In resting, unstimulated cells, importins α cannot recognize NLS motifs in SRTFs due to their shielding, e.g. by inhibitor of NF-κB (IκBα) or by posttranslational modifications, e.g. phosphorylation of NFAT (see FIG. 1). Following cell activation-induced degradation of IκBα and/or other modifications (e.g. dephosphorylation), NLS motifs are exposed on SRTFs, allowing them to complex with importins α and β for nuclear translocation. Once inside the nucleus, free SRTFs bind to their cognate sites in DNA and initiate gene transcription, leading to genome-wide reprogramming. Thus, the transition of immune and non-immune cells from a resting to an activated state is controlled by the nuclear translocation of transcription factors to the nucleus. During this process, SRTFs activate a plethora of genes that encode inflammatory cytokines and chemokines, signal transducers (cyclooxygenase, nitric oxide synthase), and cell adhesion molecules, a truly massive response known as a genomic storm.

In turn, multiple signaling networks of cytokines and chemokines contribute to the mechanism of adult and neonatal sepsis by aggravating microvascular injury initiated by microbial agents that ignite a genomic storm. Notably, NTM alone improves bacterial clearance and hematologic indices of polymicrobial adult sepsis but is not sufficient to improve survival without concomitant antimicrobial therapy. Conversely, antimicrobial therapy alone is not sufficient to reduce lethality in an experimental anthrax sepsis model. Thus, combination of antimicrobial therapy and normalization of sepsis-induced dysregulation of gene regulatory networks by NTM led to significant improvement in survival in two distinct experimental sepsis models based on airway and peritoneal routes of infection.

In most studies of clinical sepsis in adult patients, increased levels of selectins are indicators of sepsis, with higher levels generally indicating increased severity of disease and mortality. However, in some studies, survival has been correlated with higher plasma levels of soluble selectins. It is postulated that the lower levels of soluble adhesion molecules in patients with worse outcomes are due to disrupted shedding, with elevated levels of cell surface adhesion molecules retained on the cell surface. However, those studies evaluated sL- and sE-selectins in the context of rampant infection, not infection where inflammatory signaling has been ameliorated. Indeed, selectins are necessary for effective neutrophil recruitment. In the experiments, lower soluble levels of sE- and sP-selectins in NTM-treated mice indicate reduced endothelial damage due to ameliorated inflammatory signaling, not aberrant shedding. This is also supported by lower levels of sL-selectin and decreased leukocyte extravasation into livers of NTM-treated animals. Additionally, increased bacterial clearance in NTM-treated animals precludes the need for increased extravasation to fight infection. Therefore the results are not contradictory, but instead indicate that reduced inflammatory signaling due to inhibited nuclear translocation prevents activation of the cells that shed selectins. Thus, the complex modulation of several SRTFs by NTM leads to normalized signaling through multiple inflammatory signaling pathways, not just an effect on any one of them (see FIG. 1).

This study of nuclear transport signaling in the mechanism of polymicrobial sepsis opens up a new avenue for exploring innovative approaches to restore the complex balance of pro- and anti-inflammatory mechanisms in blood and vascular systems that allows for successful recovery from infections mediated by microbial inflammation including their end-stage, sepsis. However, further studies are needed to examine the mechanisms at play in resolving sepsis. The discovery of lipid mediators, such as resolvin D1, that regulate inflammation, reduce apoptosis of lymphocytes, and promote a return to homeostasis is one of many emerging approaches in sepsis research. Notably, resolvin D1 inhibits ER stress-induced apoptosis of liver cells by reducing sterol regulatory element-binding protein (SREBP) 1 expression and caspase 3 activity. As recently demonstrated in a model of hyperlipidemia, the bi-functional NTM cSN50.1 used herein also modulates nuclear transport of SREBPs and carbohydrate-responsive element binding protein (ChREPB), transcription factors responsible for lipid and carbohydrate homeostasis, respectively, in addition to reducing nuclear transport of SRTFs. Thus, NTM-regulated expression and action of SREBPs and ChREBP, as well as reduction of endotoxin-induced caspase 3/7 activity, offer potential mechanisms for suppression of glycogenolysis in early sepsis and cytoprotective effects in the later, immunosuppressive stage of sepsis. A study characterizing metabolomic, proteomic and clinical variables in sepsis survival and death delineated robust and reproducible differences in host responses to sepsis in survivors and non-survivors. Glycolysis, gluconeogenesis and the citric acid cycle differed prominently between survivors and non-survivors of community-acquired sepsis, and accumulation of carnitine esters with medium- or short-chain fatty acids and branched-chain amino acids were the most pronounced biochemical markers identified in non-survivors. Taken together, the experimental study identifies nuclear transport as a key step in the development of irreversible microvascular injury that contributes to the lethal outcome of polymicrobial sepsis. Targeting the nuclear transport of proinflammatory transcription factors, as demonstrated in this study, and metabolic transactivators documented elsewhere, attenuates the initiation and progression of microbial and metabolic inflammation that underlie sepsis.

c) Materials and Methods (1) Peptide Synthesis and Purification

Highly soluble cell-penetrating NTM peptide cSN50.1, was synthesized, purified, and filter-sterilized as described elsewhere.

(2) Animals, Infection and Sample Collection

Eight week-old female C57Bl/6J mice (Jackson Laboratories) were used in all experiments and randomly assigned to treatment groups. For survival and blood cytokine/chemokine analyses, all mice were injected i.p. with 2 mg CS/g body weight (5.5×108 CFU/kg). CS was freshly prepared for each experiment as described by Wynn et al. Briefly, healthy 6 week-old female mice were euthanized less than 2 weeks after arrival from the vendor, their cecum isolated and the cecal contents ("gut microbiome") extruded, weighed, and suspended in 5% dextrose at a concentration of 80 mg/ml (standardized Cecal Slurry, CS). NTM peptide cSN50.1 was dissolved in sterile water and diluted with sterile physiological saline to a final concentration of 3.3 mg/ml in 0.45% w/v of NaCl. Mice were given NTM (cSN50.1 peptide, 0.66 mg/injection), or vehicle (0.45% w/v of NaCl) by i.p. injections of 0.2 ml at 30 min before and 30 min, 1.5 h, 2.5 h, 3.5 h, 6 h, 9 h, and 12 h after CS challenge. NTM injections continued every 6 h until 54 h, then every 12 h until sacrifice at 168 h (7 days post-CS). Antibiotic therapy with meropenem (25 mg/kg administered s.c.) was begun at 12 h post-CS and continued every 12 h until sacrifice. Blood samples (~40 µL) were collected from the saphenous vein in EDTA before and at 2 h, 6 h, 12 h and 24 h post-CS challenge. Plasma was separated by centrifugation and stored at −80° C. Mice were closely monitored for survival throughout the experimental period.

For analyses of blood cell populations, bacterial colonization of blood and organs, and SRTFs in liver nuclear extracts, CS was prepared and administered as described above at a dose of 1.8 mg CS/g body weight. Control mice were given a sham dose of 5% dextrose alone adjusted to their body weight. CS groups were treated with 7 i.p. injections of cSN50.1 or vehicle prepared as described above. Mice were euthanized by isoflurane inhalation 12 h after CS/sham injection. Whole blood was collected in EDTA from the retro-orbital plexus. Lung, spleen and liver were harvested, snap-frozen in liquid nitrogen, and stored at −80° C., or for bacterial counts, dipped briefly in 70% ethanol then put on ice in 0.5 ml sterile PBS. One liver lobe was fixed in 10% formalin for histological analysis. Liver was perfused with sterile PBS before transfer to liquid nitrogen or formalin. Blood cell populations were determined in freshly collected whole blood by automated complete blood count in the Translational Pathology Shared Resource at Vanderbilt University.

(3) Nuclear Extract Preparation and Immunoblotting

Nuclear extracts were prepared from frozen livers. Briefly, liver pieces were disrupted in a Dounce hand homogenizer on ice without NP-40 and nuclei pelleted at 4000×g for 1 minute before extract preparation. Extracts from 5 mice in each group (sham-infected, CS-infected+vehicle and CS-infected+cSN50.1) were analyzed for nuclear import of SRTFs by quantitative immunoblotting using polyclonal goat anti-cFos (Santa Cruz), monoclonal mouse anti-Y701 phosphorylated STAT1 (Becton-Dickinson) and polyclonal rabbit anti-NF-κBp50 and anti-NF-κB p65 (Abcam) on a Licor Odyssey Infrared Imaging System. Mouse monoclonal anti-TATA binding protein (TBP, Abcam) was used to measure TBP as a nuclear loading control for normalization.

(4) Bacterial Cultures

Whole blood (50 µl) was diluted 1:1 with sterile PBS. Left lung and whole spleen were homogenized in 0.5 ml sterile PBS, and serial dilutions made in sterile PBS. Samples were plated on Tryptic Soy Agar+5% sheep's blood. Colonies were counted after overnight incubation at 37° C. and results reported in CFU per milliliter of blood, or organ homogenate.

(5) Cytokine/Chemokine Assays

A cytometric bead array (BD BioSciences) was used to measure IL-6, IL-10, MCP-1, TNFα, and soluble E- and L-selectins in murine blood plasma following the manufacturer's protocol and analyzed in the Flow Cytometry Core at Vanderbilt University. MN-γ and Soluble P-selectin were measured in murine blood plasma by ELISA (ThermoFisher Scientific and R&D Systems, respectively).

(6) Histological Analyses

Tissues collected for microscopic analysis were fixed overnight in formalin then processed routinely, embedded in paraffin, sectioned at 5 microns and mounted on charged slides. Slides for pathology evaluation were stained with PAS or immunostained for neutrophils in the Translational Pathology Shared Resource at Vanderbilt University. Immunohistochemistry for neutrophils was performed on the Leica Bond Max (Leica Biosystems Inc. Buffalo Grove, IL) using Epitope Retrieval 2 solution for 20 minutes. Slides were incubated with anti-Neutrophil Marker (Cat. ab2557, Abcam, Cambridge, MA) for one hour at a 1:2000 dilution and then incubated in a rabbit anti-rat secondary (BA-4001, Vector Laboratories, Inc.) for 15 minutes at a 1:200 dilution. The Bond Polymer Refine Detection system was used for visualization. Immunostained slides were imaged at 20× magnification to a resolution of 0.5 μm/pixel using a high throughput Leica SCN400 Slide Scanner automated digital image system from Leica Microsystems. Upper and lower thresholds for color, saturation, intensity, size, roundness, and axis length were set for both blue Hematoxylin staining of nuclei and for brown DAB reaction products. Thus, brown (DAB) positive cells can be distinguished from blue (Hematoxylin only) negative cells. The percentage of positive brown (DAB-positive) stained cells was calculated as a total analyzed number of positive cells divided by total number cells in the section of liver. Whole slide imaging and quantification of immunostaining were performed in the Digital Histology Shared Resource at Vanderbilt University Medical Center.

(7) Statistics

GraphPad Prism software was used for statistical analyses. Blood cell counts, bacterial counts in blood, lung homogenates and liver homogenates, neutrophil immunostaining, plasma levels of sP-selectin at 24 h and mean time to death were compared using the non-parametric Mann-Whitney U test. Cytokine, chemokine, sL-selectin and sE selectin levels in plasma collected from the same animals at different time points were evaluated by repeated measures two-way ANOVA with Sidak's post-test. SRTFs in nuclear extracts were analyzed by t test. Survival data were plotted as Kaplan-Meier survival curves and analyzed by the log-rank test. Data are presented as the means±SEM and p values of <0.05 were considered significant.

D. References

Hawiger J, Veach R A, Zienkiewicz J (2015) New paradigms in sepsis: from prevention to protection of failing microcirculation. J Thromb Haemost 13: 1743-1756.

Kumar A, Roberts D, Wood K E, Light B, Parrillo J E, Sharma S, et al. (2006) Duration of hypotension before initiation of effective antimicrobial therapy is the critical determinant of survival in human septic shock. Crit Care Med 34: 1589-1596.

Charalambous B M, Leung M H (2012) Pneumococcal sepsis and nasopharyngeal carriage. Curr Opin Pulm Med 18: 222-227.

Schroeder M, Brooks B D, Brooks A E (2017) The Complex Relationship between Virulence and Antibiotic Resistance. Genes (Basel) 8.

Kroger C, Kary S C, Schauer K, Cameron A D (2016) Genetic Regulation of Virulence and Antibiotic Resistance in *Acinetobacter baumannii*. Genes (Basel) 8.

Opal S M (2010) New perspectives on immunomodulatory therapy for bacteraemia and sepsis. Int J Antimicrob Agents 36 Suppl 2: S70-73.

Beutler B (2004) Innate immunity: an overview. Mol Immunol 40: 845-859.

Hawiger J (2001) Innate immunity and inflammation: a transcriptional paradigm. Immunol Res 23: 99-109.

Xiao W, Mindrinos M N, Seok J, Cuschieri J, Cuenca A G, Gao H, et al. (2011) A genomic storm in critically injured humans. J Exp Med 208: 2581-2590.

DiGiandomenico A, Veach R A, Zienkiewicz J, Moore D J, Wylezinski L S, Hutchens M A, et al. (2014) The "genomic storm" induced by bacterial endotoxin is calmed by a nuclear transport modifier that attenuates localized and systemic inflammation. PLoS One 9: e110183.

Angus D C, van der Poll T (2013) Severe sepsis and septic shock. N Engl J Med 369: 2063.

Hawiger J, Musser J M (2011) How to approach genome wars in sepsis? Crit Care 15: 1007.

Talcott B, Moore M S (1999) Getting across the nuclear pore complex. Trends Cell Biol 9: 312-318.

Weis K (2003) Regulating access to the genome. Nucleocytoplasmic transport throughout the cell cycle. Cell 112: 441-451.

Bohrer H, Qiu F, Zimmermann T, Zhang Y, Jllmer T, Mannel D, et al. (1997) Role of NFkappaB in the mortality of sepsis. J Clin Invest 100: 972-985.

Ye X, Ding J, Zhou X, Chen G, Liu S F (2008) Divergent roles of endothelial NF-kappaB in multiple organ injury and bacterial clearance in mouse models of sepsis. J Exp Med 205: 1303-1315.

Liu G, Ye X, Miller E J, Liu S F (2014) NF-kappaB-to-AP-1 switch: a mechanism regulating transition from endothelial bather injury to repair in endotoxemic mice. Sci Rep 4: 5543.

Zienkiewicz J, Armitage A, Hawiger J (2013) Targeting nuclear import shuttles, importins/karyopherins alpha by a peptide mimicking the NFkappaB1/p50 nuclear localization sequence. J Am Heart Assoc 2: e000386.

Liu Y, Major A S, Zienkiewicz J, Gabriel C L, Veach R A, Moore D J, et al. (2013) Nuclear transport modulation reduces hypercholesterolemia, atherosclerosis, and fatty liver. J Am Heart Assoc 2: e000093.

Veach R A, Liu D, Yao S, Chen Y, Liu X Y, Downs S, et al. (2004) Receptor/transporter-independent targeting of functional peptides across the plasma membrane. J Biol Chem 279: 11425-11431.

Torgerson T R, Colosia A D, Donahue J P, Lin Y Z, Hawiger J (1998) Regulation of NF-kappa B, AP-1, NFAT, and STAT1 nuclear import in T lymphocytes by noninvasive delivery of peptide carrying the nuclear localization sequence of NF-kappa B p50. J Immunol 161: 6084-6092.

Liu D, Liu X Y, Robinson D, Burnett C, Jackson C, Seele L, et al. (2004) Suppression of Staphylococcal Enterotoxin B-induced Toxicity by a Nuclear Import Inhibitor. J Biol Chem 279: 19239-19246.

Liu D, Li C, Chen Y, Burnett C, Liu X Y, Downs S, et al. (2004) Nuclear import of proinflammatory transcription factors is required for massive liver apoptosis induced by bacterial lipopolysaccharide. J Biol Chem 279: 48434-48442.

Liu X Y, Robinson D, Veach R A, Liu D, Timmons S, Collins R D, et al. (2000) Peptide-directed suppression of a pro-inflammatory cytokine response. J Biol Chem 275: 16774-16778.

Vincent J L, Rello J, Marshall J, Silva E, Anzueto A, Martin C D, et al. (2009) International study of the prevalence and outcomes of infection in intensive care units. JAMA 302: 2323-2329.

Wynn J L, Scumpia P O, Delano M J, O'Malley K A, Ungaro R, Abouhamze A, et al. (2007) Increased mortality and altered immunity in neonatal sepsis produced by generalized peritonitis. Shock 28: 675-683.

Baran-Marszak F, Feuillard J, Najjar I, Le Clorennec C, Bechet J M, Dusanter-Fourt I, et al. (2004) Differential roles of STAT1alpha and STAT1beta in fludarabine-induced cell cycle arrest and apoptosis in human B cells. Blood 104: 2475-2483.

Wallington J, Ning J, Titheradge M A (2008) The control of hepatic glycogen metabolism in an in vitro model of sepsis. Mol Cell Biochem 308: 183-192.

Frazier W J, Wang X, Wancket L M, Li X A, Meng X, Nelin L D, et al. (2009) Increased inflammation, impaired bacterial clearance, and metabolic disruption after gram-negative sepsis in Mkp-1-deficient mice. J Immunol 183: 7411-7419.

Qiu G, Wang C, Smith R, Harrison K, Yin K (2001) Role of IFN-gamma in bacterial containment in a model of intra-abdominal sepsis. Shock 16: 425-429.

Herwig M C, Tsokos M, Hermanns M I, Kirkpatrick C J, Müller A M (2013) Vascular Endothelial Cadherin Expression in Lung Specimens of Patients with Sepsis-Induced Acute Respiratory Distress Syndrome and Endothelial Cell Cultures. Pathobiology 80: 245-251.

Reddy R C, Chen G H, Newstead M W, Moore T, Zeng X, Tateda K, et al. (2001) Alveolar macrophage deactivation in murine septic peritonitis: role of interleukin 10. Infect Immun 69: 1394-1401.

Hui P, Cook D J, Lim W, Fraser G A, Arnold D M (2011) The frequency and clinical significance of thrombocytopenia complicating critical illness: a systematic review. Chest 139: 271-278.

Steeber D A, Tang M L, Green N E, Zhang X Q, Sloane J E, Tedder T F (1999) Leukocyte entry into sites of inflammation requires overlapping interactions between the L-selectin and ICAM-1 pathways. J Immunol 163: 2176-2186.

Lush C W, Cepinskas G, Sibbald W J, Kvietys P R (2001) Endothelial E- and P-selectin expression in iNOS-deficient mice exposed to polymicrobial sepsis. Am J Physiol Gastrointest Liver Physiol 280: G291-297.

Ley K, Bullard D C, Arbones M L, Bosse R, Vestweber D, Tedder T F, et al. (1995) Sequential contribution of L- and P-selectin to leukocyte rolling in vivo. J Exp Med 181: 669-675.

Kishimoto T K, Jutila M A, Berg E L, Butcher E C (1989) Neutrophil Mac-1 and MEL-14 adhesion proteins inversely regulated by chemotactic factors. Science 245: 1238-1241.

Leeuwenberg J F, Smeets E F, Neefjes J J, Shaffer M A, Cinek T, Jeunhomme T M, et al. (1992) E-selectin and intercellular adhesion molecule-1 are released by activated human endothelial cells in vitro. Immunology 77: 543-549.

Haraldsen G, Kvale D, Lien B, Farstad I N, Brandtzaeg P (1996) Cytokine-regulated expression of E-selectin, intercellular adhesion molecule-1 (ICAM-1), and vascular cell adhesion molecule-1 (VCAM-1) in human microvascular endothelial cells. J Immunol 156: 2558-2565.

Duerschmied D, Bode C, Ahrens I (2014) Immune functions of platelets. Thromb Haemost 112: 678-691.

Veach R A, Zienkiewicz J, Collins R D, Hawiger J (2012) Lethality in a murine model of pulmonary anthrax is reduced by combining nuclear transport modifier with antimicrobial therapy. PLoS One 7: e30527.

Deng M, Scott M J, Loughran P, Gibson G, Sodhi C, Watkins S, et al. (2013) Lipopolysaccharide clearance, bacterial clearance, and systemic inflammatory responses are regulated by cell type-specific functions of TLR4 during sepsis. J Immunol 190: 5152-5160.

Wolff S M (1973) Biological effects of bacterial endotoxins in man. J Infect Dis 128: Suppl:259-264.

Davis C E, Arnold K (1974) Role of meningococcal endotoxin in meningococcal purpura. J Exp Med 140: 159-171.

Wynn J L, Wilson C S, Hawiger J, Scumpia P O, Marshall A F, Liu J H, et al. (2016) Targeting IL-17A attenuates neonatal sepsis mortality induced by IL-18. Proc Natl Acad Sci USA 113: E2627-2635.

Zonneveld R, Martinelli R, Shapiro N I, Kuijpers T W, Plotz F B, Carman C V (2014) Soluble adhesion molecules as markers for sepsis and the potential pathophysiological discrepancy in neonates, children and adults. Crit Care 18: 204.

Ley K (2003) The role of selectins in inflammation and disease. Trends Mol Med 9: 263-268.

Buckley C D, Gilroy D W, Serhan C N (2014) Proresolving lipid mediators and mechanisms in the resolution of acute inflammation. Immunity 40: 315-327.

Jung T W, Hwang H J, Hong H C, Choi H Y, Yoo H J, Baik S H, et al. (2014) Resolvin D1 reduces ER stress-induced apoptosis and triglyceride accumulation through JNK pathway in HepG2 cells. Mol Cell Endocrinol 391: 30-40.

Langley R J, Tsalik E L, van Velkinburgh J C, Glickman S W, Rice B J, Wang C, et al. (2013) An integrated clinico-metabolomic model improves prediction of death in sepsis. Sci Transl Med 5: 195ra195. 28

What is claimed is:

1. A method of treating microbial inflammation in a subject comprising administering to the subject a therapeutically effective amount of an anti-microbial agent and a composition comprising a Nuclear Transport Modifier (NTM); wherein the microbial inflammation is caused by a bacterial infection; wherein the bacteria causing the bacterial infection is not *Bacillus anthracis*; and wherein the NTM comprises the sequence as set forth in SEQ ID NO: 2, SEQ ID NO: 5, SEQ ID NO: 6, SEQ ID NO: 7, SEQ ID NO: 8, SEQ ID NO: 9, or SEQ ID NO: 16.

2. The method of claim 1, wherein the NTM composition does not comprise the anti-microbial agent.

3. The method of claim 1, wherein the NTM composition comprises the anti-microbial agent.

4. The method of claim 1, wherein the microbial inflammation is acute inflammation, subacute inflammation, chronic inflammation, organ-specific inflammation, systemic inflammation, or sepsis.

5. The method of claim 1, wherein the microbial inflammation is localized in the blood, brain, aural cavities, sinuses, upper respiratory tract, lungs, heart, bone marrow, spleen, liver, kidneys, genito-urinary tract, bladder, stomach, intestines, skin, eyes, teeth, and/or gingiva.

6. The method of claim 1, wherein the bacterial infection is an infection with a bacteria selected from the group consisting of *Mycobacterium tuberculosis, Mycobacterium bovis, Mycobacterium bovis* strain BCG, BCG substrains, *Mycobacterium avium, Mycobacterium intracellular, Mycobacterium africanum, Mycobacterium kansasii, Mycobacterium marinum, Mycobacterium ulcerans, Mycobacterium avium* subspecies *paratuberculosis, Nocardia asteroides,* other *Nocardia* species, *Legionella pneumophila,* other *Legionella* species, *Actinobacteria baumanii, Salmonella typhi, Salmonella enterica,* other *Salmonella* species, *Shigella boydii, Shigella dysenteriae, Shigella sonnei, Shigella flexneri,* other *Shigella* species, *Yersinia pestis, Pasteurella haemolytica, Pasteurella multocida,* other *Pasteurella* species, *Actinobacillus pleuropneumoniae, Listeria monocytogenes, Listeria ivanovii, Brucella abortus,* other *Brucella* species, *Cowdria ruminantium, Borrelia burgdorferi, Bordetella avium, Bordetella pertussis, Bordetella bronchiseptica, Bordetella trematum, Bordetella hinzii, Bordetella pteri, Bordetella parapertussis, Bordetella ansorpii,* other *Bordetella* species, *Burkholderia mallei, Burkholderia psuedomallei, Burkholderia cepacian, Chlamydia pneumoniae, Chlamydia trachomatis, Chlamydia psittaci, Coxiella burnetii, Rickettsial* species, *Ehrlichia* species, *Staphylococcus aureus, Staphylococcus epidermidis, Streptococcus pneumoniae, Streptococcus pyogenes, Streptococcus agalactiae, Escherichia coli, Vibrio cholerae, Campylobacter* species, *Neisseria meningitidis, Neisseria gonorrhea, Pseudomonas aeruginosa,* other *Pseudomonas* species, *Haemophilus influenzae, Haemophilus ducreyi,* other *Hemophilus* species, *Clostridium tetani,* other *Clostridium* species, *Yersinia enterolitica,* and other *Yersinia* species.

* * * * *

SEQUENCE LISTING

<160> NUMBER OF SEQ ID NOS: 16

<210> SEQ ID NO 1
<211> LENGTH: 29
<212> TYPE: PRT
<213> ORGANISM: Artificial Sequence
<220> FEATURE:
<223> OTHER INFORMATION: Synthetic construct

```
<400> SEQUENCE: 1

Ala Ala Val Ala Leu Leu Pro Ala Val Leu Leu Ala Leu Leu Ala Pro
1               5                   10                  15

Cys Tyr Val Gln Arg Lys Arg Gln Lys Leu Met Pro Cys
            20                  25

<210> SEQ ID NO 2
<211> LENGTH: 28
<212> TYPE: PRT
<213> ORGANISM: Artificial Sequence
<220> FEATURE:
<223> OTHER INFORMATION: Synthetic construct

<400> SEQUENCE: 2

Ala Ala Val Ala Leu Leu Pro Ala Val Leu Leu Ala Leu Leu Ala Pro
1               5                   10                  15

Cys Val Gln Arg Lys Arg Gln Lys Leu Met Pro Cys
            20                  25

<210> SEQ ID NO 3
<211> LENGTH: 29
<212> TYPE: PRT
<213> ORGANISM: Artificial Sequence
<220> FEATURE:
<223> OTHER INFORMATION: Synthetic construct; Xaa is any amino acid or
      is absent
<220> FEATURE:
<221> NAME/KEY: misc_feature
<222> LOCATION: (1)..(4)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid
<220> FEATURE:
<221> NAME/KEY: misc_feature
<222> LOCATION: (14)..(16)
<223> OTHER INFORMATION: Xaa can be any naturally occurring amino acid
<220> FEATURE:
<221> NAME/KEY: misc_feature
<222> LOCATION: (17)..(19)
<223> OTHER INFORMATION: Xaa can be any naturally occurring amino acid
<220> FEATURE:
<221> NAME/KEY: misc_feature
<222> LOCATION: (23)..(26)
<223> OTHER INFORMATION: Xaa can be any naturally occurring amino acid
<220> FEATURE:
<221> NAME/KEY: misc_feature
<222> LOCATION: (27)..(29)
<223> OTHER INFORMATION: Xaa can be any naturally occurring amino acid

<400> SEQUENCE: 3

Xaa Xaa Xaa Xaa Leu Leu Pro Xaa Xaa Leu Leu Ala Leu Leu Ala Pro
1               5                   10                  15

Xaa Xaa Xaa Gln Arg Lys Arg Gln Lys Xaa Xaa Xaa Xaa
            20                  25

<210> SEQ ID NO 4
<211> LENGTH: 29
<212> TYPE: PRT
<213> ORGANISM: Artificial Sequence
<220> FEATURE:
<223> OTHER INFORMATION: Synthetic construct; Xaa is any amino acid or
      is absent
<220> FEATURE:
<221> NAME/KEY: misc_feature
<222> LOCATION: (1)..(4)
<223> OTHER INFORMATION: Xaa can be any naturally occurring amino acid
<220> FEATURE:
<221> NAME/KEY: misc_feature
```

```
<222> LOCATION: (8)..(9)
<223> OTHER INFORMATION: Xaa can be any naturally occurring amino acid
<220> FEATURE:
<221> NAME/KEY: misc_feature
<222> LOCATION: (18)..(19)
<223> OTHER INFORMATION: Xaa can be any naturally occurring amino acid
<220> FEATURE:
<221> NAME/KEY: misc_feature
<222> LOCATION: (26)..(28)
<223> OTHER INFORMATION: Xaa can be any naturally occurring amino acid

<400> SEQUENCE: 4

Xaa Xaa Xaa Xaa Leu Leu Pro Xaa Xaa Leu Leu Ala Leu Leu Ala Pro
1               5                   10                  15

Cys Xaa Xaa Gln Arg Lys Arg Gln Lys Xaa Xaa Xaa Cys
            20                  25

<210> SEQ ID NO 5
<211> LENGTH: 28
<212> TYPE: PRT
<213> ORGANISM: Artificial Sequence
<220> FEATURE:
<223> OTHER INFORMATION: Synthetic construct; Xaa is any amino acid or
      is absent
<220> FEATURE:
<221> NAME/KEY: misc_feature
<222> LOCATION: (1)..(4)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid
<220> FEATURE:
<221> NAME/KEY: misc_feature
<222> LOCATION: (25)..(27)
<223> OTHER INFORMATION: Xaa can be any naturally occurring amino acid

<400> SEQUENCE: 5

Xaa Xaa Xaa Xaa Leu Leu Pro Xaa Xaa Leu Leu Ala Leu Leu Ala Pro
1               5                   10                  15

Cys Xaa Gln Arg Lys Arg Gln Lys Xaa Xaa Xaa Cys
            20                  25

<210> SEQ ID NO 6
<211> LENGTH: 29
<212> TYPE: PRT
<213> ORGANISM: Artificial Sequence
<220> FEATURE:
<223> OTHER INFORMATION: Synthetic construct; Xaa is any amino acid or
      is absent
<220> FEATURE:
<221> NAME/KEY: misc_feature
<222> LOCATION: (1)..(4)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid
<220> FEATURE:
<221> NAME/KEY: misc_feature
<222> LOCATION: (17)..(19)
<223> OTHER INFORMATION: Xaa can be any naturally occurring amino acid
<220> FEATURE:
<221> NAME/KEY: misc_feature
<222> LOCATION: (26)..(29)
<223> OTHER INFORMATION: Xaa can be any naturally occurring amino acid

<400> SEQUENCE: 6
```

```
Xaa Xaa Xaa Xaa Leu Leu Pro Xaa Xaa Leu Leu Ala Val Leu Ala Pro
1               5                   10                  15

Xaa Xaa Xaa Gln Arg Lys Arg Gln Lys Xaa Xaa Xaa Xaa
            20                  25
```

<210> SEQ ID NO 7
<211> LENGTH: 28
<212> TYPE: PRT
<213> ORGANISM: Artificial Sequence
<220> FEATURE:
<223> OTHER INFORMATION: Synthetic construct

<400> SEQUENCE: 7

```
Ala Ala Val Ala Leu Leu Pro Ala Val Leu Leu Ala Val Leu Ala Pro
1               5                   10                  15

Cys Val Gln Arg Lys Arg Gln Lys Leu Met Pro Cys
            20                  25
```

<210> SEQ ID NO 8
<211> LENGTH: 29
<212> TYPE: PRT
<213> ORGANISM: Artificial Sequence
<220> FEATURE:
<223> OTHER INFORMATION: Synthetic construct; Xaa is any amino acid or
      is absent
<220> FEATURE:
<221> NAME/KEY: misc_feature
<222> LOCATION: (1)..(4)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid
<220> FEATURE:
<221> NAME/KEY: misc_feature
<222> LOCATION: (17)..(19)
<223> OTHER INFORMATION: Xaa can be any naturally occurring amino acid
<220> FEATURE:
<221> NAME/KEY: misc_feature
<222> LOCATION: (26)..(29)
<223> OTHER INFORMATION: Xaa can be any naturally occurring amino acid

<400> SEQUENCE: 8

```
Xaa Xaa Xaa Xaa Leu Leu Pro Xaa Xaa Leu Leu Ala Val Leu Ala Pro
1               5                   10                  15

Xaa Xaa Xaa Gln Arg Asp Glu Gln Lys Xaa Xaa Xaa Xaa
            20                  25
```

<210> SEQ ID NO 9
<211> LENGTH: 28
<212> TYPE: PRT
<213> ORGANISM: Artificial Sequence
<220> FEATURE:
<223> OTHER INFORMATION: Synthetic construct

<400> SEQUENCE: 9

```
Ala Ala Val Ala Leu Leu Pro Ala Val Leu Leu Ala Val Leu Ala Pro
1               5                   10                  15

Cys Val Gln Arg Asp Glu Gln Lys Leu Met Pro Cys
            20                  25
```

<210> SEQ ID NO 10
<211> LENGTH: 10
<212> TYPE: PRT
<213> ORGANISM: Artificial Sequence
<220> FEATURE:
<223> OTHER INFORMATION: Synthetic construct

```
<400> SEQUENCE: 10

Val Gln Arg Lys Arg Gln Lys Leu Met Pro
1               5                   10

<210> SEQ ID NO 11
<211> LENGTH: 10
<212> TYPE: PRT
<213> ORGANISM: Artificial Sequence
<220> FEATURE:
<223> OTHER INFORMATION: Synthetic construct

<400> SEQUENCE: 11

Val Gln Arg Asp Glu Gln Lys Leu Met Pro
1               5                   10

<210> SEQ ID NO 12
<211> LENGTH: 12
<212> TYPE: PRT
<213> ORGANISM: Artificial Sequence
<220> FEATURE:
<223> OTHER INFORMATION: Synthetic construct

<400> SEQUENCE: 12

Cys Val Gln Arg Lys Arg Gln Lys Leu Met Pro Cys
1               5                   10

<210> SEQ ID NO 13
<211> LENGTH: 26
<212> TYPE: PRT
<213> ORGANISM: Artificial Sequence
<220> FEATURE:
<223> OTHER INFORMATION: Synthetic construct

<400> SEQUENCE: 13

Ala Ala Val Ala Leu Leu Pro Ala Val Leu Leu Ala Leu Leu Ala Pro
1               5                   10                  15

Val Gln Arg Lys Arg Gln Lys Leu Met Pro
            20                  25

<210> SEQ ID NO 14
<211> LENGTH: 7
<212> TYPE: PRT
<213> ORGANISM: Homo sapiens

<400> SEQUENCE: 14

Ala Ala Val Ala Leu Leu Pro
1               5

<210> SEQ ID NO 15
<211> LENGTH: 9
<212> TYPE: PRT
<213> ORGANISM: Homo sapiens

<400> SEQUENCE: 15

Ala Val Leu Leu Ala Leu Leu Ala Pro
1               5

<210> SEQ ID NO 16
<211> LENGTH: 28
<212> TYPE: PRT
<213> ORGANISM: Artificial Sequence
<220> FEATURE:
<223> OTHER INFORMATION: Synthetic construct

<400> SEQUENCE: 16
```

-continued

```
Ala Ala Val Ala Leu Leu Pro Ala Val Leu Leu Ala Leu Leu Ala Pro
1               5                   10                  15

Cys Val Gln Arg Asp Glu Gln Lys Leu Met Pro Cys
                20                  25
```